(12) United States Patent
O'Connor et al.

(10) Patent No.: US 12,116,637 B2
(45) Date of Patent: Oct. 15, 2024

(54) COMPOSITIONS AND METHODS FOR DETECTING AND TREATING HIGH GRADE SUBTYPES OF UTERINE CANCER

(71) Applicant: The Regents of the University of Michigan, Ann Arbor, MI (US)

(72) Inventors: Caitlin O'Connor, Ann Arbor, MI (US); Goutham Narla, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 51 days.

(21) Appl. No.: 17/380,876

(22) Filed: Jul. 20, 2021

(65) Prior Publication Data
US 2022/0049315 A1    Feb. 17, 2022

Related U.S. Application Data

(60) Provisional application No. 63/056,279, filed on Jul. 24, 2020.

(51) Int. Cl.
    *C12Q 1/6886* (2018.01)
(52) U.S. Cl.
    CPC ...... *C12Q 1/6886* (2013.01); *C12Q 2600/112* (2013.01); *C12Q 2600/156* (2013.01)
(58) Field of Classification Search
    CPC ............ C12Q 1/6886; C12Q 2600/112; C12Q 2600/156
    See application file for complete search history.

(56) References Cited

U.S. PATENT DOCUMENTS

| | | | |
|---|---|---|---|
| 4,946,778 A | 8/1990 | Ladner et al. | |
| 5,118,801 A | 6/1992 | Lizardi et al. | |
| 5,210,015 A | 5/1993 | Gelfand et al. | |
| 5,242,828 A | 9/1993 | Bergstrom et al. | |
| 5,312,728 A | 5/1994 | Lizardi et al. | |
| 5,538,848 A | 7/1996 | Livak et al. | |
| 5,695,934 A | 12/1997 | Brenner | |
| 5,714,330 A | 2/1998 | Brenner et al. | |
| 5,719,060 A | 2/1998 | Hutchens et al. | |
| 5,750,341 A | 5/1998 | Macevicz | |
| 5,866,336 A | 2/1999 | Nazarenko et al. | |
| 5,912,148 A | 6/1999 | Eggerding | |
| 6,117,635 A | 9/2000 | Nazarenko et al. | |
| 6,124,137 A | 9/2000 | Hutchens et al. | |
| 6,130,073 A | 10/2000 | Eggerding | |
| 6,210,891 B1 | 4/2001 | Nyren et al. | |
| 6,225,047 B1 | 5/2001 | Hutchens et al. | |
| 6,258,568 B1 | 7/2001 | Nyren | |
| 6,306,597 B1 | 10/2001 | Macevicz | |
| 6,329,209 B1 | 12/2001 | Wagner et al. | |
| 6,432,360 B1 | 8/2002 | Church | |
| 6,485,944 B1 | 11/2002 | Church et al. | |
| 6,511,803 B1 | 1/2003 | Church et al. | |
| 6,537,749 B2 | 3/2003 | Kuimelis et al. | |
| 6,555,813 B1 | 4/2003 | Beecher et al. | |
| 6,579,719 B1 | 6/2003 | Hutchens et al. | |
| 6,706,162 B1 | 3/2004 | Voss et al. | |
| 6,787,308 B2 | 9/2004 | Balasubramanian et al. | |
| 6,818,395 B1 | 11/2004 | Quake et al. | |
| 6,833,246 B2 | 12/2004 | Balasubramanian | |
| 6,897,072 B1 | 5/2005 | Rich et al. | |
| 6,911,345 B2 | 6/2005 | Quake et al. | |
| 6,969,488 B2 | 11/2005 | Bridgham et al. | |
| 7,045,366 B2 | 5/2006 | Huang et al. | |
| 7,115,400 B1 | 10/2006 | Adessi et al. | |
| 7,169,560 B2 | 1/2007 | Lapidus et al. | |
| 7,282,337 B1 | 10/2007 | Harris | |
| 7,329,492 B2 | 2/2008 | Hardin et al. | |
| 7,482,120 B2 | 1/2009 | Buzby | |
| 7,501,245 B2 | 3/2009 | Quake et al. | |
| 7,668,697 B2 | 2/2010 | Volkov et al. | |
| 8,043,493 B2 | 10/2011 | Inaba et al. | |
| 9,982,304 B2 | 5/2018 | Vogelstein et al. | |
| 2003/0032043 A1 | 2/2003 | Pohl et al. | |
| 2003/0218130 A1 | 11/2003 | Boschetti et al. | |
| 2005/0130173 A1 | 6/2005 | Leamon et al. | |
| 2008/0241951 A1 | 10/2008 | Battulga et al. | |
| 2009/0026082 A1 | 1/2009 | Rothberg et al. | |
| 2009/0035777 A1 | 2/2009 | Kokoris et al. | |
| 2009/0127589 A1 | 5/2009 | Rothberg et al. | |
| 2010/0137143 A1 | 6/2010 | Rothberg et al. | |
| 2010/0188073 A1 | 7/2010 | Rothberg et al. | |
| 2010/0197507 A1 | 8/2010 | Rothberg et al. | |
| 2010/0301398 A1 | 12/2010 | Rothberg et al. | |
| 2014/0294729 A1 | 10/2014 | Gupta et al. | |
| 2017/0312334 A1 | 11/2017 | Gadek | |
| 2018/0045727 A1* | 2/2018 | Spetzler ........... G01N 33/57434 | |

FOREIGN PATENT DOCUMENTS

| | | |
|---|---|---|
| EP | 0235726 | 9/1987 |
| WO | WO 89/011548 | 11/1989 |
| WO | WO 93/022456 | 11/1993 |
| WO | WO 00/018957 | 4/2000 |
| WO | WO 00/056934 | 9/2000 |
| WO | WO 03/040700 | 5/2003 |
| WO | WO 03/048768 | 6/2003 |
| WO | WO 03/064594 | 8/2003 |
| WO | WO 2006/084132 | 8/2006 |

OTHER PUBLICATIONS

McConechy (J Pathol 2011 223:567-573).*

(Continued)

*Primary Examiner* — Sarae L Bausch
(74) *Attorney, Agent, or Firm* — Casimir Jones, S.C.; Robert A. Goetz

(57) ABSTRACT

The present invention relates to methods and biomarkers for detection and characterization of conditions associated with aberrant function of the PPP2R1A subunit of the PP2A protein (e.g., high grade subtypes of uterine cancer) in biological samples (e.g., tissue samples, blood samples, plasma samples, cell samples, serum samples), and related methods of treatment. In particular, the present invention provides compositions and methods for characterizing a patient as having such a condition by identifying mutations in the PPP2R1A subunit of the PP2A gene or gene products, and related methods of treatment through administering to such a patient a DNA Damage Response Pathway (DDR) modulating agent (e.g., a ribonucleotide reductase inhibitor).

5 Claims, 19 Drawing Sheets

(56) References Cited

OTHER PUBLICATIONS

Grishman (Int J Gynecol Cancer 2012, 22:807-811).*
Prendergast (gynecologic Oncology, 2019, 154, 461-466).*
International Search Report and Written Opinion for PCT/US21/42385. Mailed Dec. 23, 2021. 21 pages.
Abravaya et al., Detection of point mutations with a modified ligase chain reaction (Gap-LCR). Nucleic Acids Res. Feb. 25, 1995;23(4):675-82.
Adessi et al., Solid phase DNA amplification: characterisation of primer attachment and amplification mechanisms. Nucleic Acids Res. Oct. 15, 2000;28(20):E87. 8 pages.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Aye et al., Clofarabine 5'-di and -triphosphates inhibit human ribonucleotide reductase by altering the quaternary structure of its large subunit. Proc Natl Acad Sci U S A. Jun. 14, 2011;108(24):9815-20.
Aye et al., Ribonucleotide reductase and cancer: biological mechanisms and targeted therapies. Oncogene. Apr. 16, 2015;34(16):2011-21.
Bennett et al., Toward the 1,000 dollars human genome. Pharmacogenomics. Jun. 2005;6(4):373-82.
Berger et al., A Comprehensive Pan-Cancer Molecular Study of Gynecologic and Breast Cancers. Cancer Cell. Apr. 9, 2018;33(4):690-705.e9. 47 pages.
Birren et al., Genome Analysis: Analyzing DNA, 1, Cold Spring Harbor, N.Y. 1997. TOC only. 12 pages.
Branton et al., The potential and challenges of nanopore sequencing. Nat Biotechnol. Oct. 2008;26(10):1146-53.
Brenner et al., Gene expression analysis by massively parallel signature sequencing (MPSS) on microbead arrays. Nat Biotechnol. Jun. 2000;18(6):630-4.
Burnette. "Western blotting": electrophoretic transfer of proteins from sodium dodecyl sulfate—polyacrylamide gels to unmodified nitrocellulose and radiographic detection with antibody and radioiodinated protein A. Anal Biochem. Apr. 1981;112(2):195-203.
Celik et al., Clofarabine inhibits Ewing sarcoma growth through a novel molecular mechanism involving direct binding to CD99. Oncogene. Apr. 2018;37(16):2181-2196.
Chen et al., Cancer-associated PP2A Aalpha subunits induce functional haploinsufficiency and tumorigenicity. Cancer Res. Sep. 15, 2005;65(18):8183-92.
Chen et al., Identification of specific PP2A complexes involved in human cell transformation. Cancer Cell. Feb. 2004;5(2):127-36.
Cho et al., Crystal structure of a protein phosphatase 2A heterotrimeric holoenzyme. Nature. Jan. 4, 2007;445(7123):53-7.
Chou et al., Theoretical basis, experimental design, and computerized simulation of synergism and antagonism in drug combination studies. Pharmacol Rev. Sep. 2006;58(3):621-81.
Clarke et al., Hysterectomy-Corrected Uterine Corpus Cancer Incidence Trends and Differences in Relative Survival Reveal Racial Disparities and Rising Rates of Nonendometrioid Cancers. J Clin Oncol. Aug. 1, 2019;37(22):1895-1908.
Cole et al., The EBV-Hybridoma Technique and its Application to Human Lung Cancer. Monoclonal Antibodies and Cancer Therapy, 1985. pp. 77-96.
Cote et al., Generation of human monoclonal antibodies reactive with cellular antigens. Proc Natl Acad Sci U S A. Apr. 1983;80(7):2026-30.
Cotton et al., Mutation Detection A Practical Approach. Oxford University Press, 1998. TOC only. 10 pages.
Deutscher. Maintaining protein stability. Methods Enzymol. 1990;182:83-9.
Drmanac et al., Accurate sequencing by hybridization for DNA diagnostics and individual genomics. Nat Biotechnol. Jan. 1998;16(1):54-8.

Eid et al., Real-time DNA sequencing from single polymerase molecules. Science. Jan. 2, 2009;323(5910):133-8.
Felix et al., Comparison of survival outcomes between patients with malignant mixed mullerian tumors and high-grade endometrioid, clear cell, and papillary serous endometrial cancers. Int J Gynecol Cancer. Jul. 2011;21(5):877-84.
Gebinoga et al., Comparison of self-sustained sequence-replication reaction systems. Eur J Biochem. Jan. 15, 1996;235(1-2):256-61.
Gibbs et al., Detection of single DNA base differences by competitive oligonucleotide priming. Nucleic Acids Res. Apr. 11, 1989;17(7):2437-48.
Gibson et al., The genomic landscape and evolution of endometrial carcinoma progression and abdominopelvic metastasis. Nat Genet. Aug. 2016;48(8):848-55.
Haesen et al., Recurrent PPP2R1A Mutations in Uterine Cancer Act through a Dominant-Negative Mechanism to Promote Malignant Cell Growth. Cancer Res. Oct. 1, 2016;76(19):5719-5731.
Harris et al., Single-molecule DNA sequencing of a viral genome. Science. Apr. 4, 2008;320(5872):106-9.
Heim et al., Highly sensitive detection of gene expression of an intronless gene: amplification of mRNA, but not genomic DNA by nucleic acid sequence based amplification (NASBA). Nucleic Acids Res. May 1, 1998;26(9):2250-1.
Huse et al., Generation of a Large Combinatorial Library of the Immunoglobulin Repertoire in Phage Lambda. Science. 1989; 246: 1275-1281.
Imai et al., Detection of HIV-1 RNA in heparinized plasma of HIV-1 seropositive individuals. J Virol Methods. Feb. 1992;36(2):181-4.
Jackson et al., Circumventing cellular control of PP2A by methylation promotes transformation in an Akt-dependent manner. Neoplasia. Jul. 2012;14(7):585-99.
Jeong et al., Patient derived mutation W257G of PPP2R1A enhances cancer cell migration through SRC-JNK-c-Jun pathway. Sci Rep. Jun. 7, 2016;6:27391. 12 pages.
Kalev et al., Loss of PPP2R2A inhibits homologous recombination DNA repair and predicts tumor sensitivity to PARP inhibition. Cancer Res. Dec. 15, 2012;72(24):6414-24.
Kandoth et al., Integrated genomic characterization of endometrial carcinoma. Nature. May 2, 2013;497(7447):67-73.
Kato. Impact of the next generation DNA sequencers. Int J Clin Exp Med. Jul. 8, 2009;2(2):193-202.
Kauko et al., PP2A inhibition is a druggable MEK inhibitor resistance mechanism in KRAS-mutant lung cancer cells. Sci Transl Med. Jul. 18, 2018;10(450):eaaq1093. 24 pages.
Kievits et al., NASBA isothermal enzymatic in vitro nucleic acid amplification optimized for the diagnosis of HIV-1 infection. J Virol Methods. Dec. 1991;35(3):273-86.
Kohler et al., Continuous cultures of fused cells secreting antibody of predefined specificity. Nature. Aug. 7, 1975;256(5517):495-7.
Korlach et al., Selective aluminum passivation for targeted immobilization of single DNA polymerase molecules in zero-mode waveguide nanostructures. Proc Natl Acad Sci U S A. Jan. 29, 2008;105(4):1176-81.
Kozbor et al., The production of monoclonal antibodies from human lymphocytes. Immunol Today. Mar. 1983;4(3):72-9.
Kwoh et al., Transcription-based amplification system and detection of amplified human immunodeficiency virus type 1 with a bead-based sandwich hybridization format. Proc Natl Acad Sci U S A. Feb. 1989;86(4):1173-7.
Leskela et al., Molecular Basis of Tumor Heterogeneity in Endometrial Carcinosarcoma. Cancers (Basel). Jul. 9, 2019;11(7):964. 21 pages.
Levene et al., Zero-mode waveguides for single-molecule analysis at high concentrations. Science. Jan. 31, 2003;299(5607):682-6.
Liu et al., An Integrated TCGA Pan-Cancer Clinical Data Resource to Drive High-Quality Survival Outcome Analytics. Cell. Apr. 5, 2018;173(2):400-416.e11.
Livak et al., Oligonucleotides with fluorescent dyes at opposite ends provide a quenched probe system useful for detecting PCR product and nucleic acid hybridization. PCR Methods Appl. Jun. 1995;4(6):357-62.

(56) References Cited

OTHER PUBLICATIONS

Lizardi et al., Exponential amplification of nucleic acids: new diagnostics using DNA polymerases and RNA replicases. Trends Biotechnol. Feb. 1991;9(2):53-8.
MacLean et al., Application of 'next-generation' sequencing technologies to microbial genetics. Nat Rev Microbiol. Apr. 2009;7(4):287-96.
Maniatis et al., Molecular Cloning, A Laboratory Manual, 2d, Cold Spring Harbor Laboratory Press, 1989. p. 16.54.
Margulies et al., Genome sequencing in microfabricated high-density picolitre reactors. Nature. Sep. 15, 2005;437(7057):376-80.
Maxam et al., A new method for sequencing DNA. Proc Natl Acad Sci USA. Feb. 1977;74(2):560-4.
Mitra et al., Fluorescent in situ sequencing on polymerase colonies. Anal Biochem. Sep. 1, 2003;320(1):55-65.
Moore et al., Detection and identification of Mycobacterium tuberculosis directly from sputum sediments by ligase chain reaction. J Clin Microbiol. Apr. 1998;36(4):1028-31.
Morozova et al., Applications of next-generation sequencing technologies in functional genomics. Genomics. Nov. 2008;92(5):255-64.
Morrison et al., Chimeric human antibody molecules: mouse antigen-binding domains with human constant region domains. Proc Natl Acad Sci U S A. Nov. 1984;81(21):6851-5.
Nazarenko et al., A closed tube format for amplification and detection of DNA based on energy transfer. Nucleic Acids Res. Jun. 15, 1997;25(12):2516-21.
Neuberger et al., Recombinant antibodies possessing novel effector functions. Nature. Dec. 13-19, 1984;312(5995):604-8.
Noto et al., Sprague Dawley Rag2-Null Rats Created from Engineered Spermatogonial Stem Cells Are Immunodeficient and Permissive to Human Xenografts. Mol Cancer Ther. Nov. 2018;17(11):2481-2489.
Noto et al., The SRG rat, a Sprague-Dawley Rag2/Il2rg double-knockout validated for human tumor oncology studies. PLoS One. Oct. 7, 2020;15(10):e0240169. 16 pages.
O'Connor et al., Therapeutic targeting of PP2A. Int J Biochem Cell Biol. Mar. 2018;96:182-193.
O'Connor et al., Inactivation of PP2A by a recurrent mutation drives resistance to MEK inhibitors. Oncogene. Jan. 2020;39(3):703-717.
O'Connor et al., Protein phosphatase 2A Aα regulates Aβ protein expression and stability. J Biol Chem. Apr. 12, 2019;294(15):5923-5934.
Pallas et al., Polyoma small and middle T antigens and SV40 small t antigen form stable complexes with protein phosphatase 2A. Cell. Jan. 12, 1990;60(1):167-76.
Parker. Enzymology of purine and pyrimidine antimetabolites used in the treatment of cancer. Chem Rev. Jul. 2009;109(7):2880-93.
Pennisi. Genomics. Semiconductors inspire new sequencing technologies. Science. Mar. 5, 2010;327(5970): p. 1190.
Qiu et al., A Genome-Wide Pooled shRNA Screen Identifies PPP2R2A as a Predictive Biomarker for the Response to ATR and CHK1 Inhibitors. Cancer Res. Aug. 15, 2020;80(16):3305-3318.
Rashtchian. Amplification of RNA. PCR Methods Appl. Oct. 1994;4(2):S83-91.
Ronaghi et al., Real-Time DNA Sequencing Using Detection of Pyrophosphate Release. Anal. Biochem. 1996. 242:84-89.
Ruediger et al., Mutagenesis and expression of the scaffolding Aalpha and Abeta subunits of PP2A: assays for measuring defects in binding of cancer-related Aalpha and Abeta mutants to the regulatory B and catalytic C subunits. Methods Mol Biol. 2007;365:85-99.
Ruparel et al., Design and synthesis of a 3'-O-allyl photocleavable fluorescent nucleotide as a reversible terminator for DNA sequencing by synthesis. Proc Natl Acad Sci U S A. Apr. 26, 2005;102(17):5932-7.
Sablina et al., Identification of PP2A complexes and pathways involved in cell transformation. Cancer Res. Dec. 15, 2010;70(24):10474-84.
Sablina et al., The role of PP2A A subunits in tumor suppression. Cell Adh Migr. Jul.-Sep. 2007;1(3):140-1.
Saiki et al., Analysis of enzymatically amplified beta-globin and HLA-DQ alpha DNA with allele-specific oligonucleotide probes. Nature. Nov. 13-19, 1986;324(6093):163-6.
Sanger et al., DNA sequencing with chain-terminating inhibitors. Proc Natl Acad Sci U S A. Dec. 1977;74(12):5463-7.
Sangodkar et al., All roads lead to PP2A: exploiting the therapeutic potential of this phosphatase. FEBS J. Mar. 2016;283(6):1004-24.
Shao et al., Epithelial-specific Cre/lox recombination in the developing kidney and genitourinary tract. J Am Soc Nephrol. Jul. 2002;13(7):1837-46.
Shendure et al., Accurate multiplex polony sequencing of an evolved bacterial genome. Science. Sep. 9, 2005;309(5741):1728-32.
Shi. Serine/threonine phosphatases: mechanism through structure. Cell. Oct. 30, 2009;139(3):468-84.
Shih et al., Somatic mutations of PPP2R1A in ovarian and uterine carcinomas. Am J Pathol. Apr. 2011;178(4):1442-7.
Siegel et al., Cancer statistics, 2018. CA Cancer J Clin. Jan. 2018;68(1):7-30.
Takeda et al., Construction of chimaeric processed immunoglobulin genes containing mouse variable and human constant region sequences. Nature. Apr. 4-10, 1985;314(6010):452-4.
Taylor et al., The Highly Recurrent PP2A Aα-Subunit Mutation P179R Alters Protein Structure and Impairs PP2A Enzyme Function to Promote Endometrial Tumorigenesis. Cancer Res. Aug. 15, 2019;79(16):4242-4257.
Tyagi et al., Molecular beacons: probes that fluoresce upon hybridization. Nat Biotechnol. Mar. 1996;14(3):303-8.
Urdea et al., Direct and quantitative detection of HIV-1 RNA in human plasma with a branched DNA signal amplification assay. AIDS. Nov. 1993;7 Suppl 2:S11-4.
Urick et al., Clinical actionability of molecular targets in endometrial cancer. Nat Rev Cancer. Sep. 2019;19(9):510-521.
Voelkerding et al., Next-generation sequencing: from basic research to diagnostics. Clin Chem. Apr. 2009;55(4):641-58.
Walker et al., Isothermal in vitro amplification of DNA by a restriction enzyme/DNA polymerase system. Proc Natl Acad Sci U S A. Jan. 1, 1992;89(1):392-6.
Whelan et al., Direct genotypic detection of Mycobacterium tuberculosis rifampin resistance in clinical specimens by using single-tube heminested PCR. J Clin Microbiol. Mar. 1995;33(3):556-61.
Whitcombe et al., Detection of PCR products using seDetection of PCR products using self-probing amplicons and fluorescence. Nat Biotechnol. Aug. 1999;17(8):804-7.
Wild et al., p53 suppresses type II endometrial carcinomas in mice and governs endometrial tumour aggressiveness in humans. EMBO Mol Med. Aug. 2012;4(8):808-24.
Wisitpitthaya et al., Cladribine and Fludarabine Nucleotides Induce Distinct Hexamers Defining a Common Mode of Reversible RNR Inhibition. ACS Chem Biol. Jul. 15, 2016;11(7):2021-32.
Wylie et al., Comparative evaluation of chlamydiazyme, PACE 2, and AMP-CT assays for detection of Chlamydia trachomatis in endocervical specimens Comparative evaluation of chlamydiazyme, PACE 2, and AMP-CT assays for detection of Chlamydia trachomatis in endocervical specimens. J Clin Microbiol. Dec. 1998;36(12):3488-91.
Yang et al., A public genome-scale lentiviral expression library of human ORFs. Nat Methods. Jun. 26, 2011;8(8):659-61.
Zhao et al., Landscape of somatic single-nucleotide and copy-number mutations in uterine serous carcinoma. Proc Natl Acad Sci U S A. Feb. 19, 2013;110(8):2916-21.

\* cited by examiner

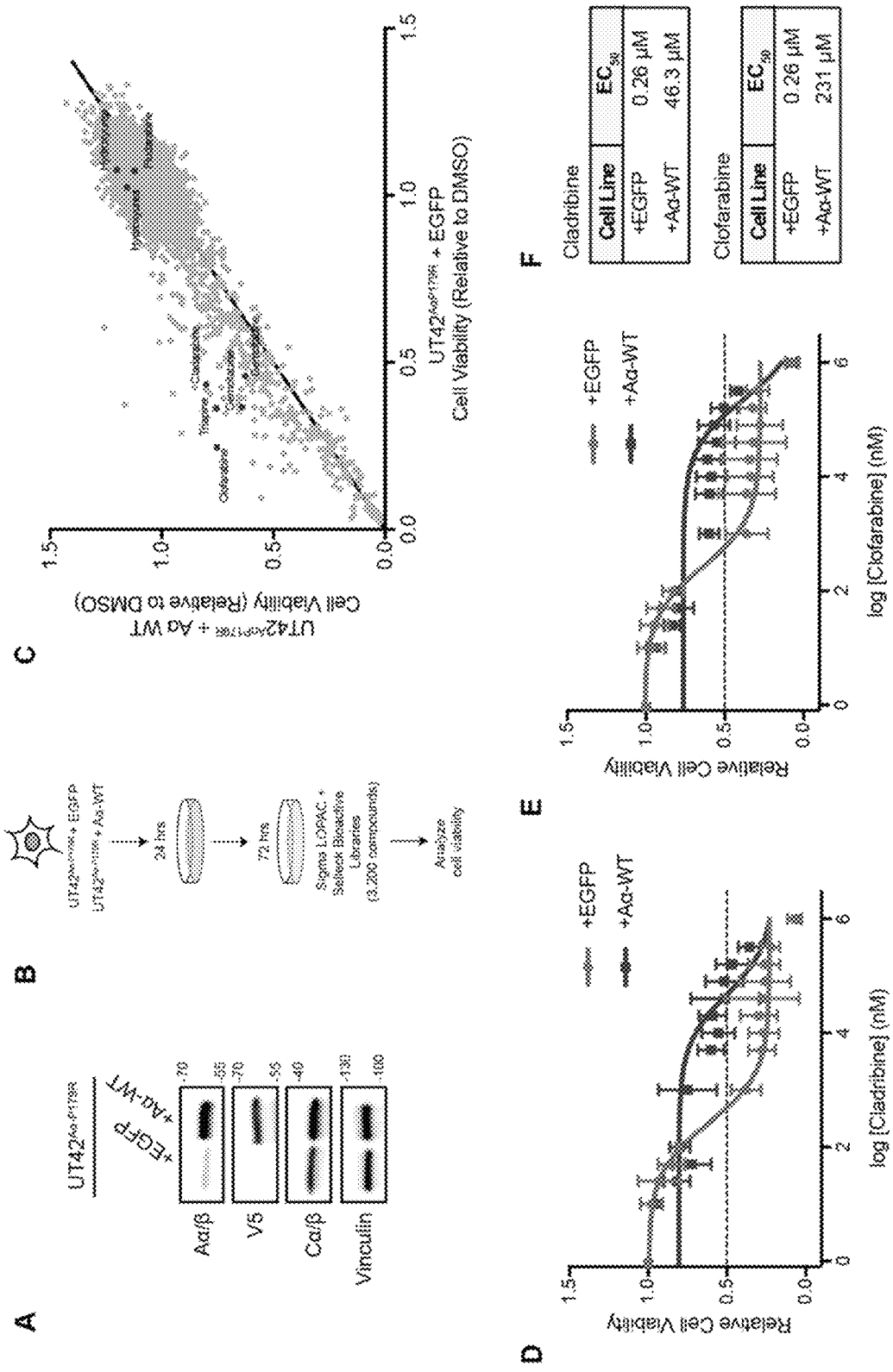
FIG. 1A-F

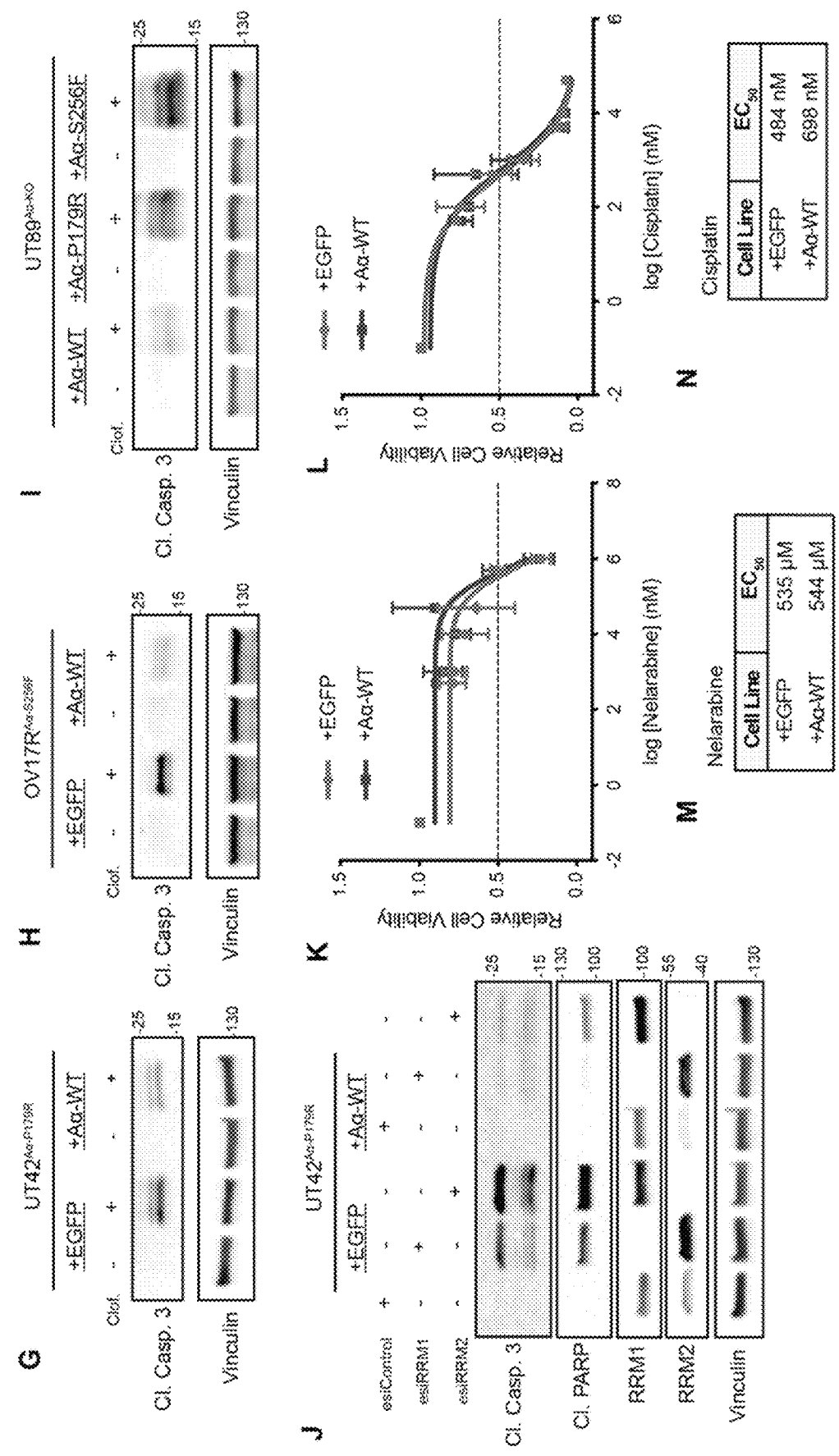
FIG. 1G-N

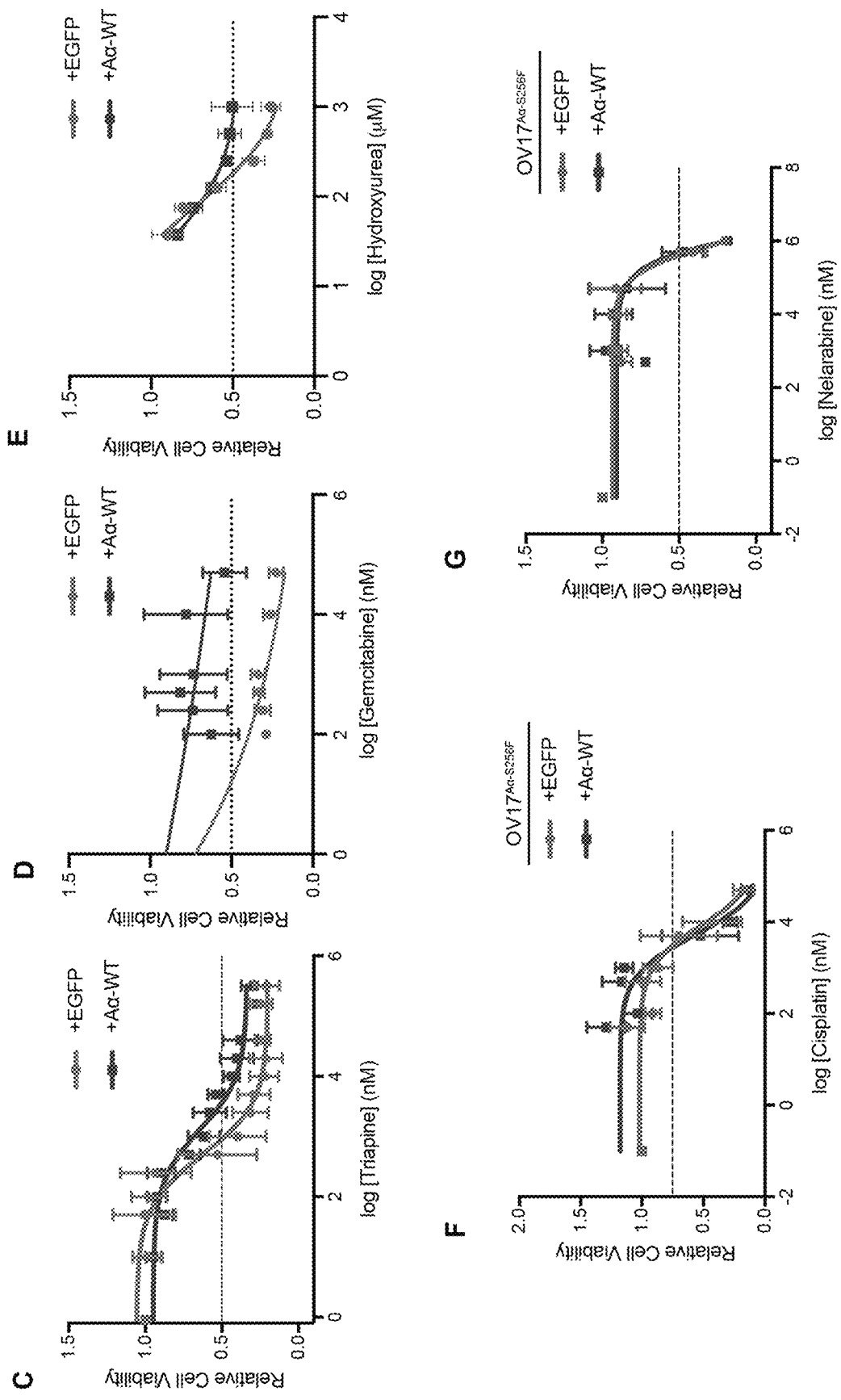
FIG. 2C-G

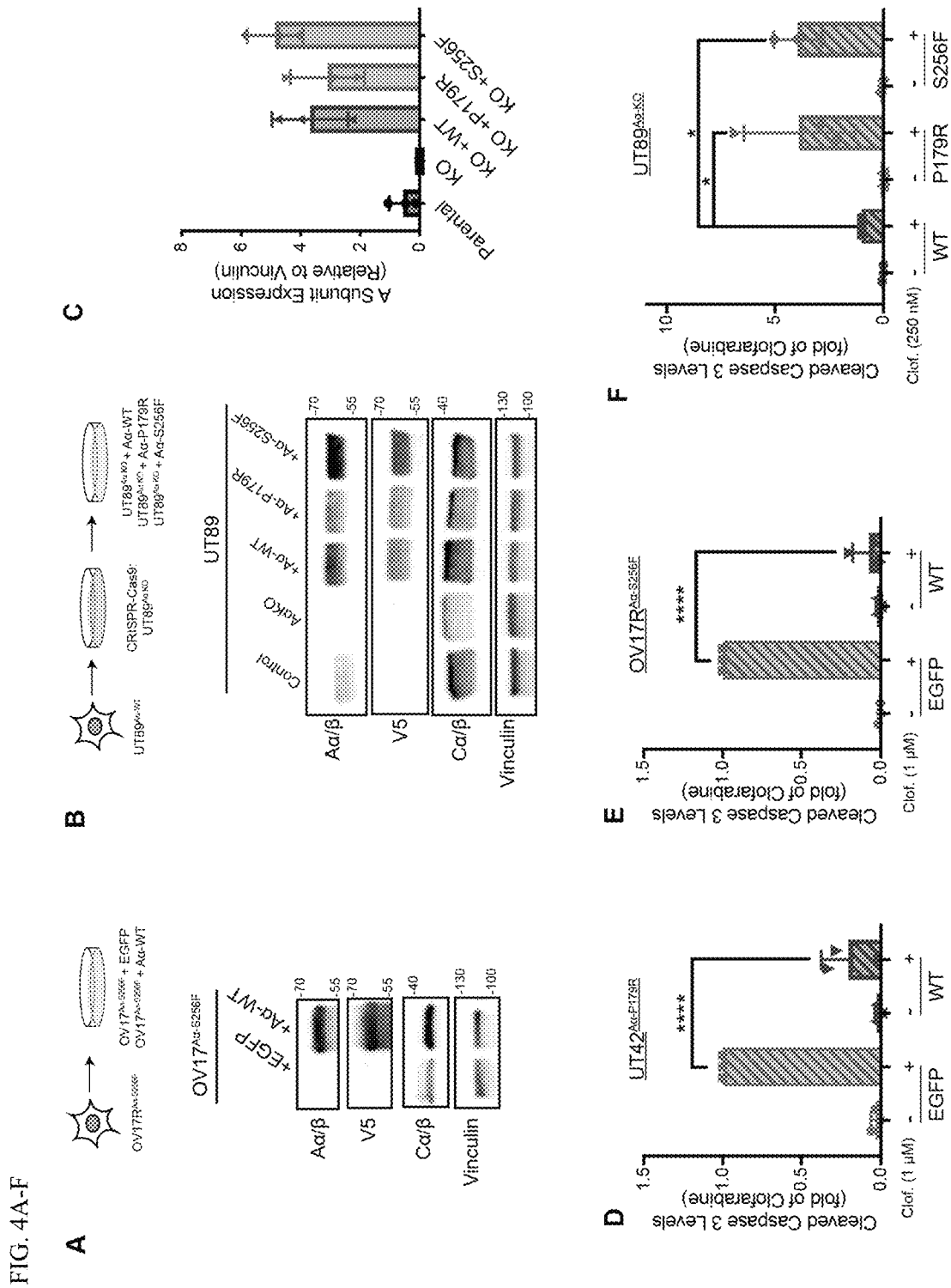
FIG. 4A-F

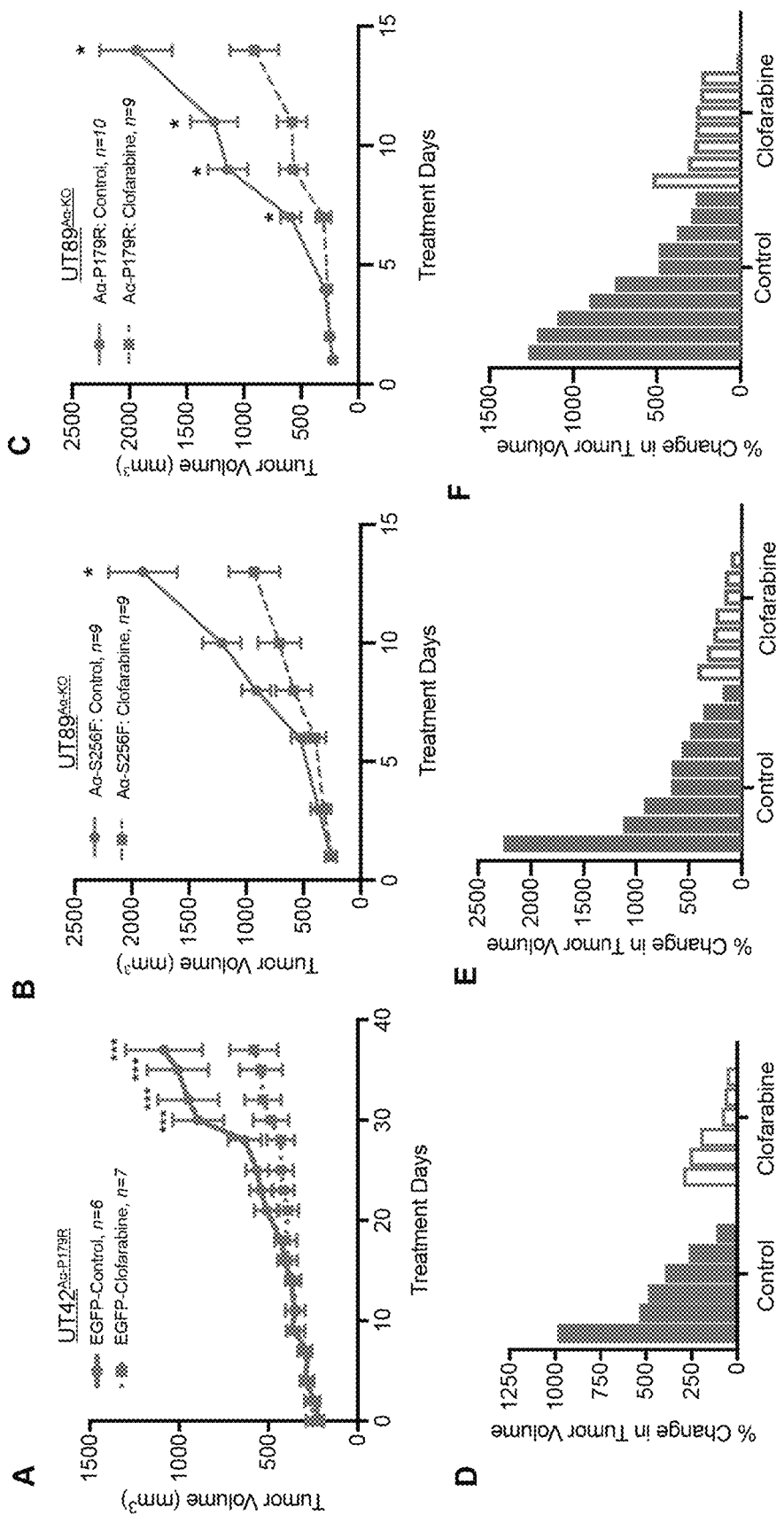
FIG. 6A-F

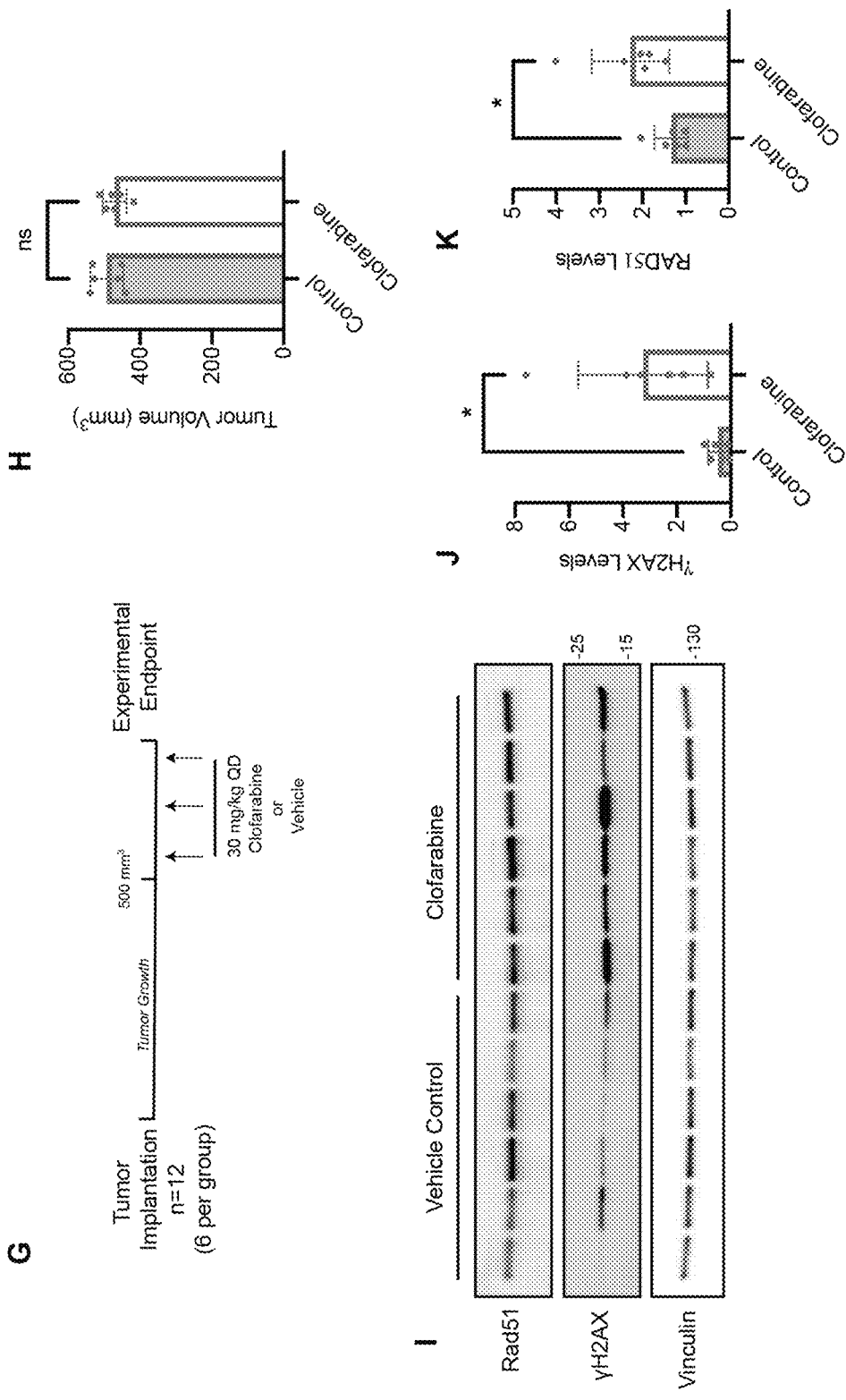
FIG. 6G-K

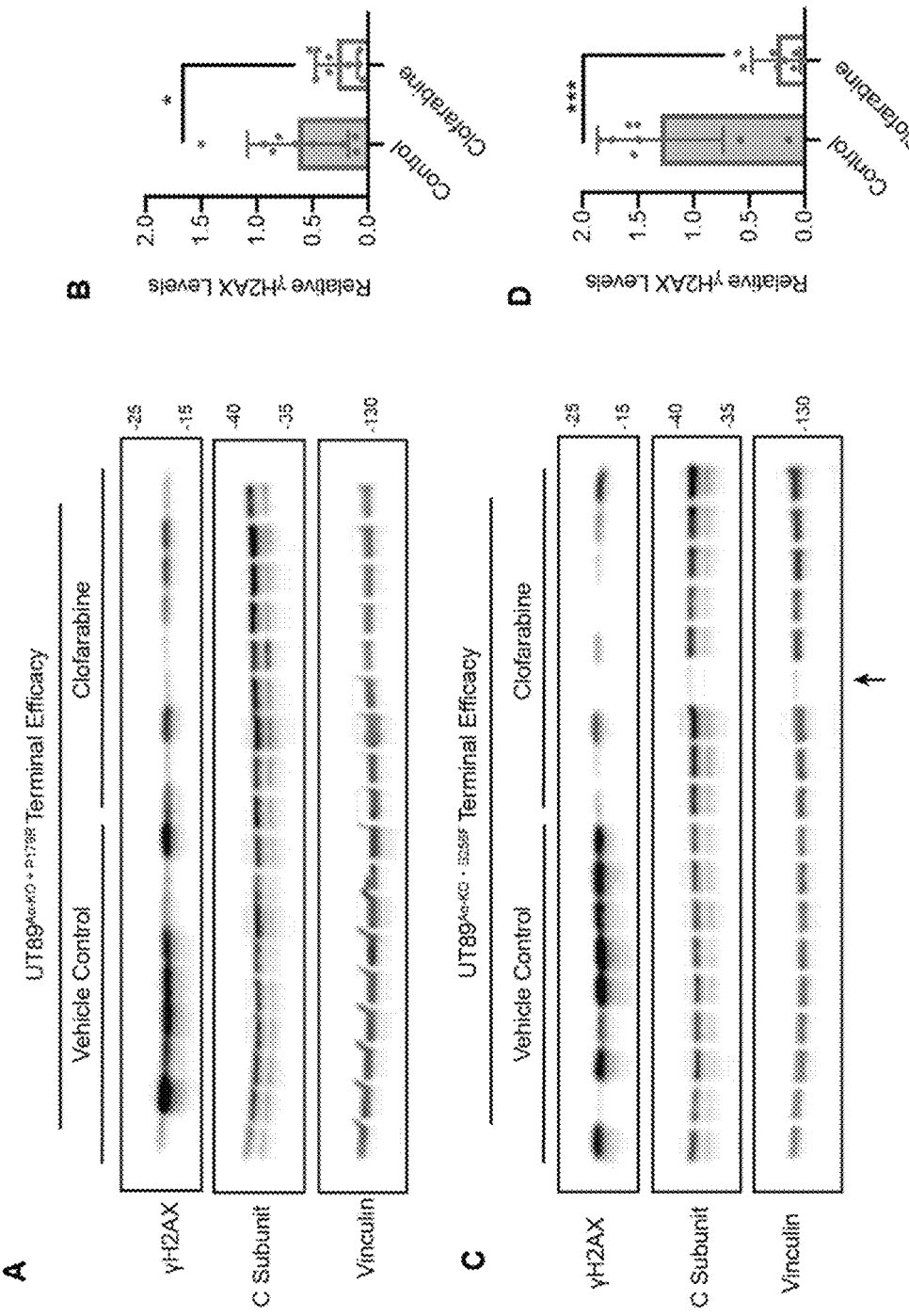

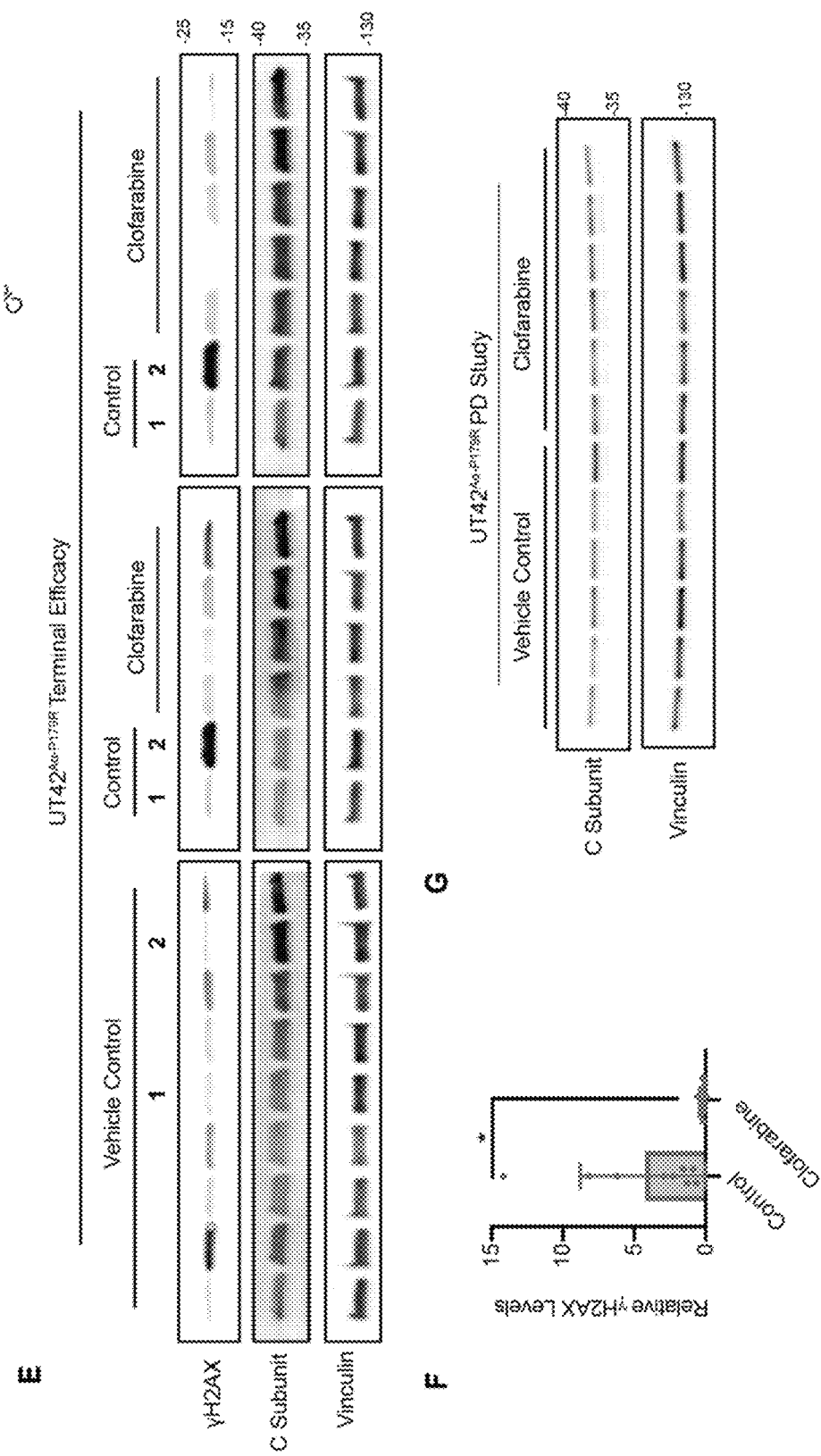
FIG. 7E-G

FIG. 8A-H
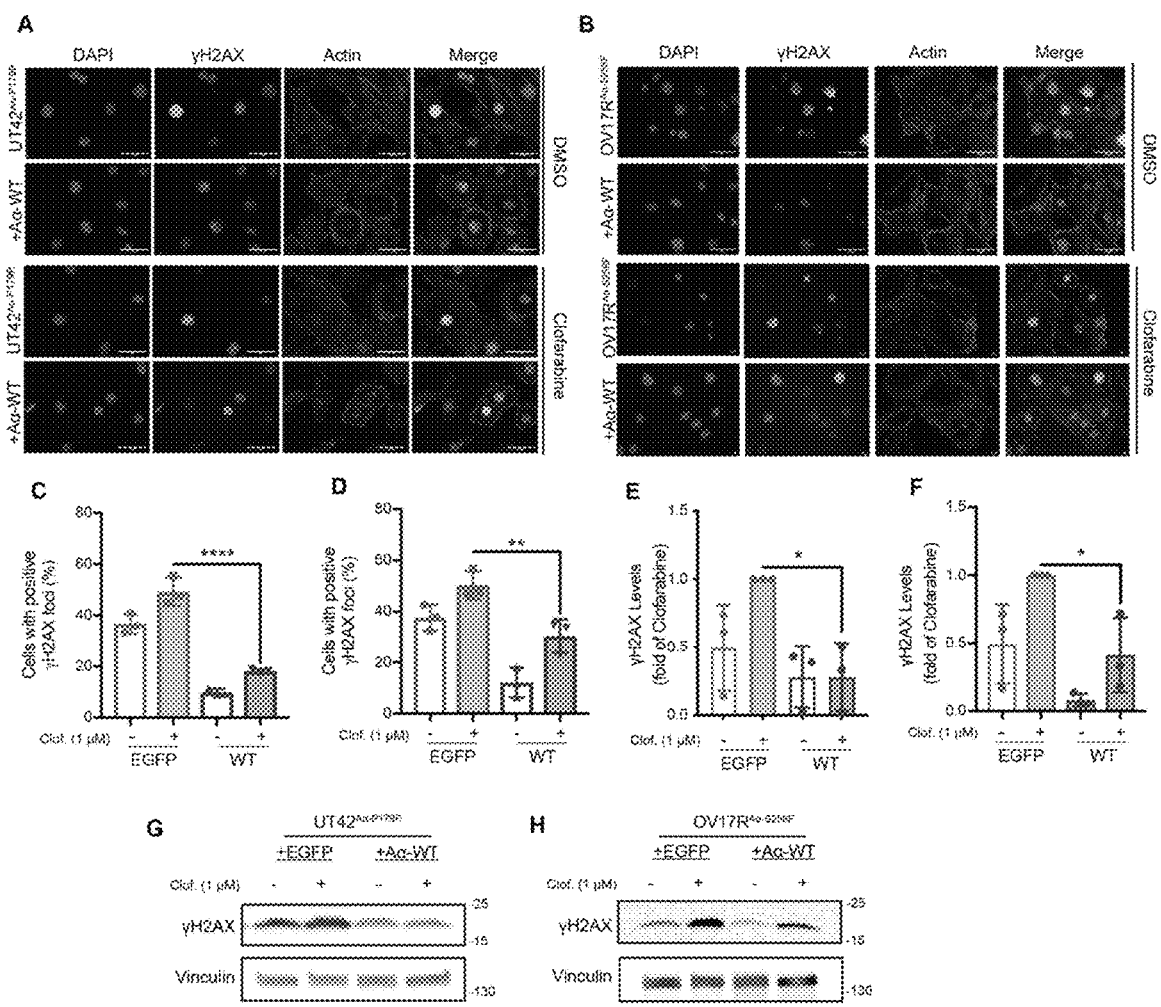

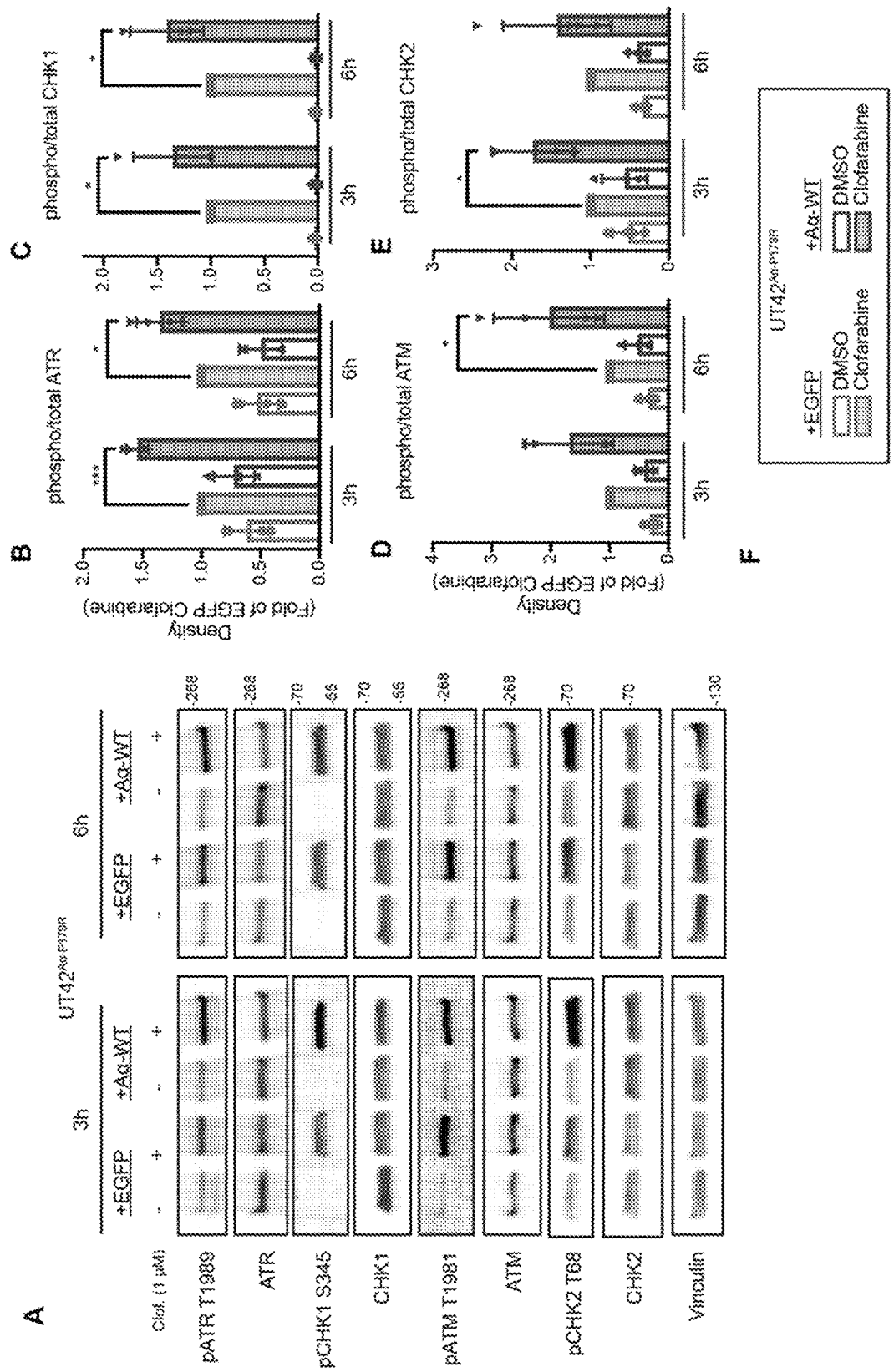
FIG. 9A-F

FIG. 9G-L
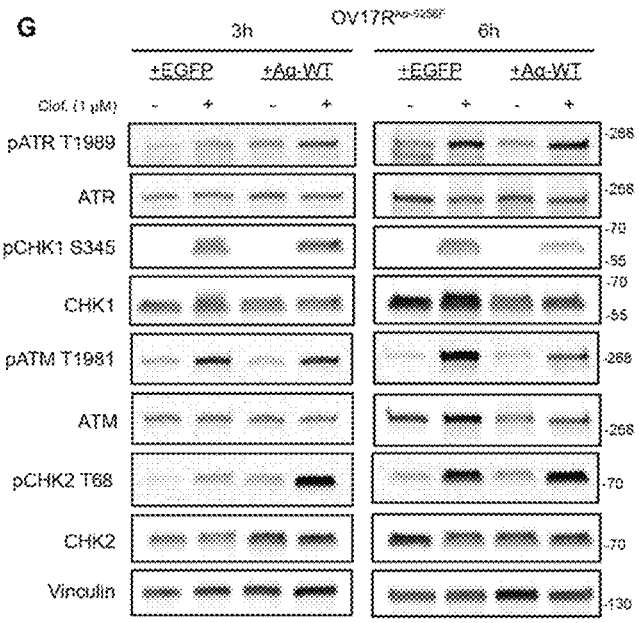
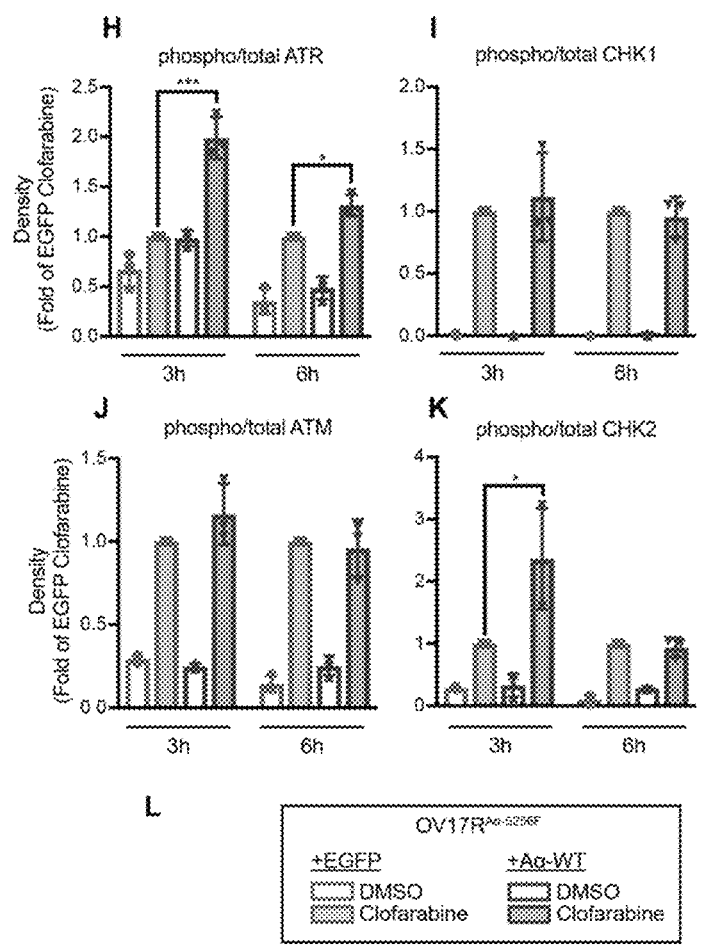

FIG. 10A-G
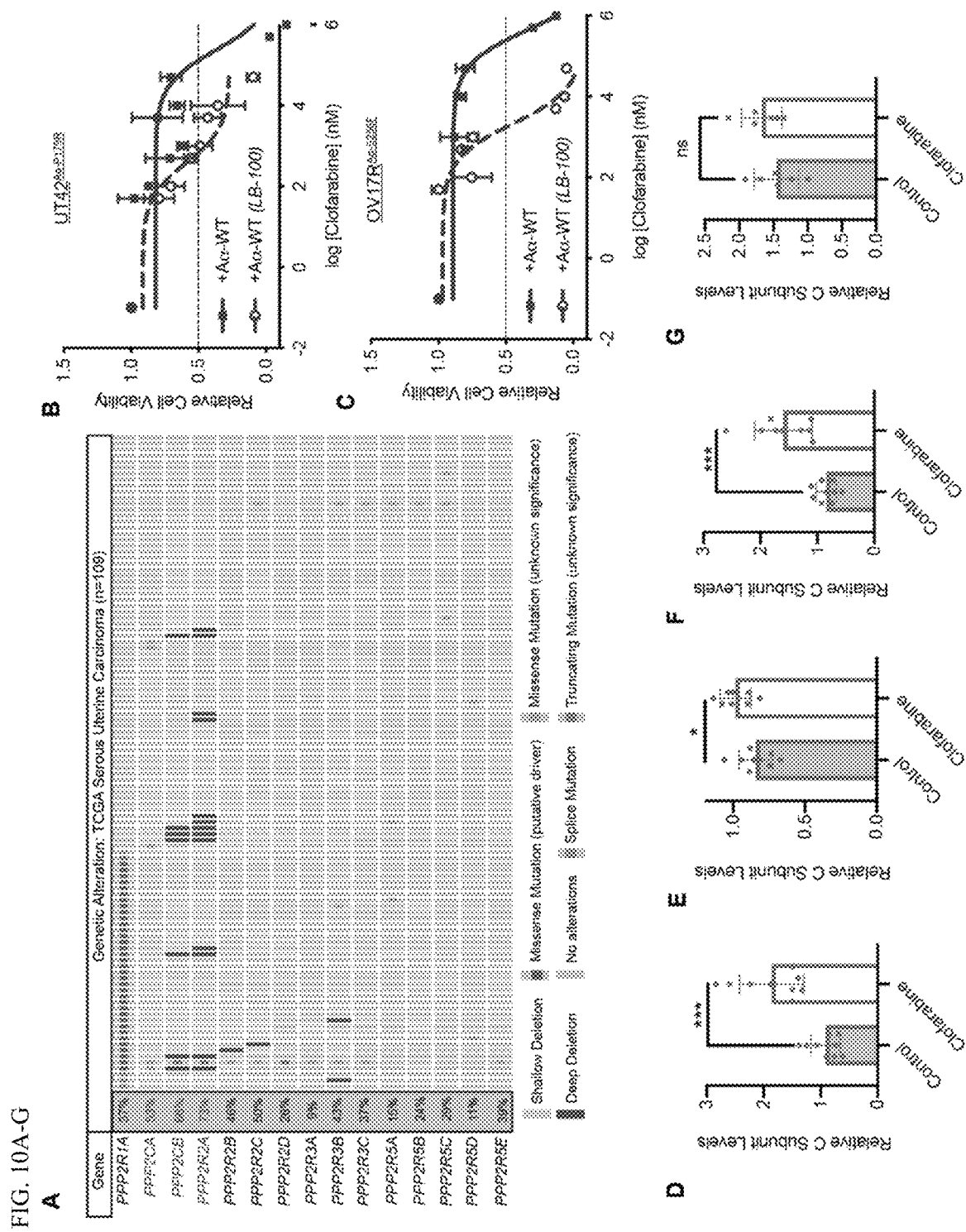

FIG. 10H-L
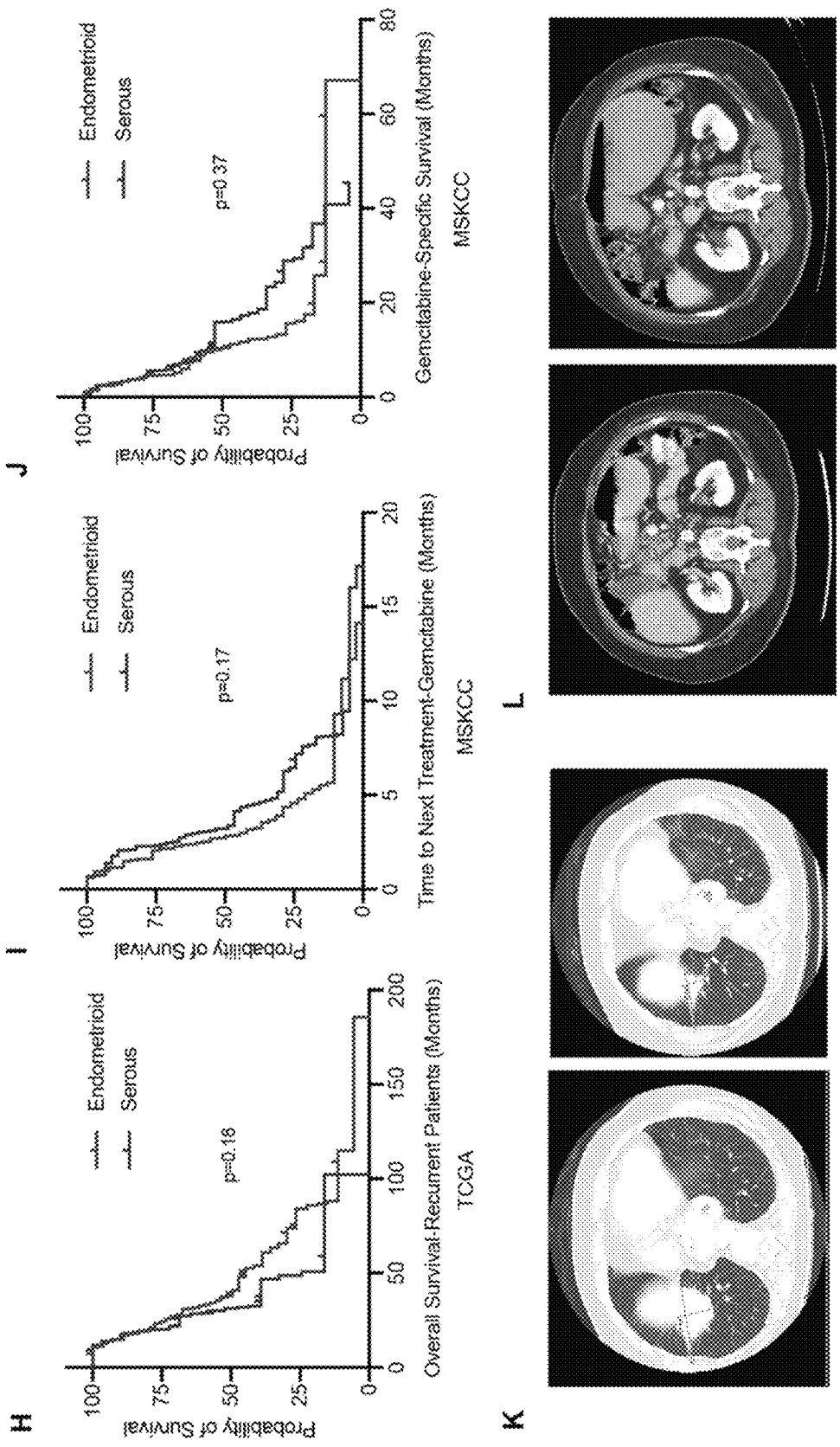

FIG. 12A-C

FIG. 13
| A | B | Neither | A not B | B not A | Both | Log2 Odds Ratio | p-Value | q-Value | Tendency |
|---|---|---|---|---|---|---|---|---|---|
| PPP2CB | PPP2R2A | 28 | 0 | 8 | 71 | >3 | <0.001 | <0.001 | Co-occurrence |
| PPP2CA | PPP2R2B | 48 | 10 | 2 | 47 | >3 | <0.001 | <0.001 | Co-occurrence |
| PPP2R3C | PPP2R5E | 58 | 8 | 10 | 31 | >3 | <0.001 | <0.001 | Co-occurrence |
| PPP2R5C | PPP2R5E | 60 | 6 | 15 | 26 | >3 | <0.001 | <0.001 | Co-occurrence |
| PPP2R3C | PPP2R5C | 59 | 16 | 9 | 23 | >3 | <0.001 | <0.001 | Co-occurrence |
| PPP2R2B | PPP2R5E | 44 | 22 | 14 | 27 | 1.948 | <0.001 | 0.015 | Co-occurrence |
| PPP2CA | PPP2R5E | 39 | 27 | 11 | 30 | 1.978 | 0.001 | 0.015 | Co-occurrence |
| PPP2R3B | PPP2R5D | 59 | 36 | 2 | 10 | >3 | 0.003 | 0.044 | Co-occurrence |
FIG. 14A
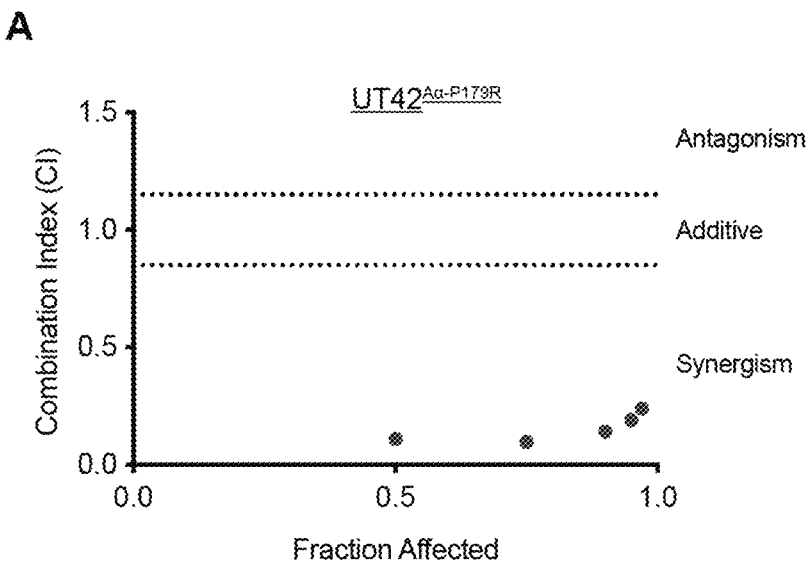
FIG. 14B
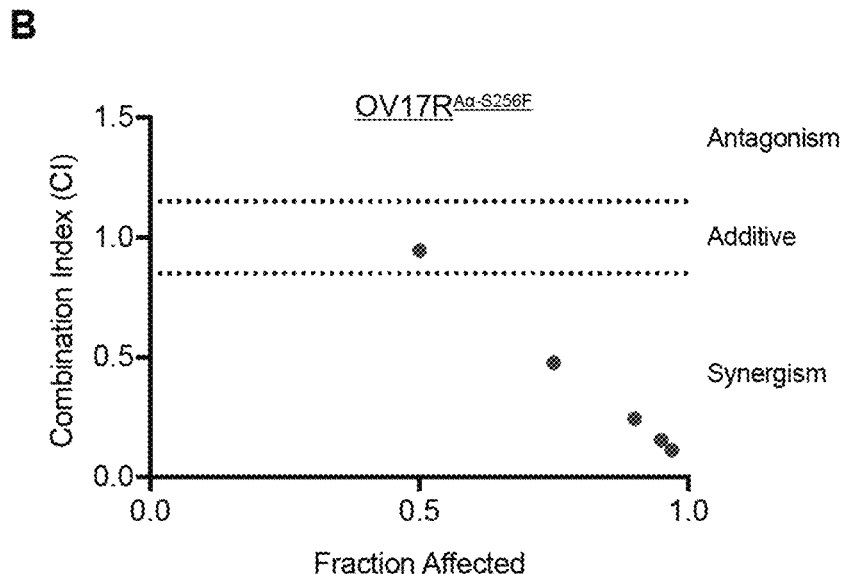

COMPOSITIONS AND METHODS FOR DETECTING AND TREATING HIGH GRADE SUBTYPES OF UTERINE CANCER

CROSS-REFERENCE TO RELATED APPLICATION

The present application claims priority to U.S. Provisional Patent Application No. 63/056,279, filed Jul. 24, 2020, which is hereby incorporated by reference in its entirety.

FIELD OF THE INVENTION

The present invention relates to methods and biomarkers for detection and characterization of conditions associated with aberrant function of the PPP2R1A subunit of the PP2A protein (e.g., high grade subtypes of uterine cancer) in biological samples (e.g., tissue samples, blood samples, plasma samples, cell samples, serum samples), and related methods of treatment. In particular, the present invention provides compositions and methods for characterizing a patient as having such a condition by identifying mutations in the PPP2R1A subunit of the PP2A gene or gene products, and related methods of treatment through administering to such a patient a DNA Damage Response Pathway (DDR) modulating agent (e.g., a ribonucleotide reductase inhibitor).

INTRODUCTION

Uterine cancer is the most common gynecologic malignancy in the United States with approximately 60,000 women diagnosed each year, according to the American Cancer Society (see, Siegel, R. L., K. D. Miller, and A. Jemal, C A Cancer J Clin, 2018. 68(1): p. 7-30). Uterine cancers can be classified into multiple histological subtypes, including uterine endometrioid carcinoma (EMC), uterine serous carcinoma (USC), uterine clear cell carcinoma (UCC) and uterine carcinosarcoma (UCS). While most cases of EMC have favorable outcomes with recurrence-free long-term survival, outcomes for the high-grade, treatment-refractory histological subtypes (USC, UCC, and UCS) remain an important clinical problem (see, Felix, A. S., et al., Int J Gynecol Cancer, 2011. 21(5): p. 877-84). While USC accounts for only 10% of uterine cancer cases, this subtype of disease represents a disproportionate 39% of deaths, with a 5-year survival of 55%. Additionally, the majority of USC cases display local dissemination and chemo resistance. Importantly, recent data correcting for the rates of hysterectomy in the United States indicates that the incidence of high-grade uterine cancers is increasing (see, Clarke, M. A., et al., J Clin Oncol, 2019 37(22): p. 1895-1908).

As such, there is an urgent need for diagnostic markers for identifying high-grade, treatment-refractory histological subtypes of uterine cancer (e.g., USC, UCC, and UCS), and improved methods for treating such types of uterine cancer. The present invention addresses such needs.

SUMMARY OF THE INVENTION

Uterine cancer is the most common gynecologic malignancy and fourth most common cause of new cancer diagnoses in women, with an over 65,000 new cases diagnosed in the United States in 2020 (1). The majority of uterine cancers are endometrial carcinomas (EMCA), malignancies of the endometrial epithelium lining. There are distinct subtypes of EMCA with markedly different prognoses: endometrioid-type carcinomas are most common (~80% of EMCA cases), frequently involve deregulated hormone signaling, and exhibit favorable outcomes; serous (USC), clear cell, and undifferentiated carcinomas do not share this etiology, rarely respond to hormone therapy, and are typically high-grade and invasive at time of diagnosis, resulting high rate of recurrence and a relatively poor prognosis (2). For recurrent cancers, after progression on upfront platinum-based chemotherapy and immunotherapy with lenvatinib and pembrolizumab viable therapeutic options remain limited. While other cancers have benefited from the development of targeted therapeutic strategies, the lack of well-characterized targetable disease drivers for USC and other high-grade EMCA tumors has generated very limited opportunities for targeted therapy to date. Progress in elucidating disease driver mechanisms will therefore be imperative to advancing new treatment options and patient outcomes.

Previous work have identified a heterozygous mutational hotspot within PPP2R1A which includes two recurrent mutations, P179R and S256F, which almost exclusively exist within the high-grade serous carcinosarcoma subtypes (3-5). Additional analysis of matched primary and metastatic tumors revealed that these mutations were trunk-biased suggesting that they constitute early events in the development of endometrial carcinoma (6). PPP2R1A encodes the gene for the Aα scaffolding subunit of the protein phosphatase 2A (PP2A), a heterotrimeric serine/threonine phosphatase and tumor suppressor (7-14). The active PP2A holoenzyme is composed of a scaffolding "A" subunit, catalytic "C" subunit, and one substrate determining "B" subunit (15,16). We have recently shown that the P179R or S256F Aα mutations result in altered assembly of the PP2A holoenzyme, specifically by disrupting the ability of PP2A B subunits and/or the catalytic C subunit to bind and contribute to uterine tumorigenesis through the inactivation of PP2A's tumor suppressive activities (3,17,18).

Experiments conducted during the course of developing embodiments for the present invention investigated whether the two hotspot mutations, P179R or S256F, in PPP2R1A would result in the identification of a druggable target. Such experiments screened 3,200 bioactive compounds and measured the cell viability of mutant and wild type patient-derived isogenic serous endometrial cancer cells to determine synthetic lethal targets in Aα mutant cells. From this screen, it was identified that cells with either recurrent mutation displayed synthetic lethality to ribonucleotide reductase (RNR) inhibitors. Furthermore, the synthetic lethality was specific to RNR inhibition, where other inducers of DNA damage, showed no differences in drug sensitivity between wild type and mutant Aα cells. Using xenograft studies in vivo, experiments demonstrated that Aα mutant tumors were also sensitive to Clofarabine given orally. Analysis of mutant and wild type treated USC cells showed that Aα mutant cells displayed impaired checkpoint signaling in response to Clofarabine treatment, and subsequently accumulated more DNA damage. Analysis of the TCGA revealed that loss or altered PP2A expression was common among all USC, and inhibitors of PP2A's catalytic activity, LB-100, sensitized PP2A wild type cells to RNR inhibition, indicating the identified synthetic lethality was PP2A dependent. Finally, retrospective analysis of a cohort of endometrial cancer patients given gemcitabine revealed that despite the expected poor outcomes, patients with USC had a trend for longer time to next treatment and overall survival when given gemcitabine when compared to those with endometrioid histology. This was in contrast to analysis of the TCGA data, where patients with recurrent uterine serous carcinomas had a worse overall survival compared to those with recurrent endometrioid carcinomas. Overall, these findings provide rationale for the use of the FDA approved class of RNR inhibitors in USC, allowing for the near-term clinical translation of these findings to patients suffering from this particularly lethal subtype of endometrial cancer.

Accordingly, the present invention relates to methods and biomarkers for detection and characterization of conditions associated with aberrant function of the PPP2R1A subunit of the PP2A protein (e.g., high grade subtypes of uterine cancer) in biological samples (e.g., tissue samples, blood samples, plasma samples, cell samples, serum samples), and related methods of treatment. In particular, the present invention provides compositions and methods for characterizing a patient as having such a condition by identifying mutations in the PPP2R1A subunit of the PP2A gene or gene products, and related methods of treatment through administering to such a patient a DNA Damage Response Pathway (DDR) modulating agent (e.g., a ribonucleotide reductase inhibitor).

In certain embodiments, the invention provides a method for assessing the presence of a condition associated with aberrant function of the PPP2R1A subunit of the PP2A protein (e.g., high grade subtypes of uterine cancer) in an individual by: a) evaluating a sample containing nucleic acids from the individual for the presence or absence of one or more mutations in the PPP2R1A subunit of the PP2A gene (e.g., a substitution mutation at the P179 (e.g., P179R) or S256 (e.g., S256F)); and b) identifying the individual as having a condition associated with aberrant function of the PPP2R1A subunit of the PP2A protein (e.g., high grade subtypes of uterine cancer) when the PPP2R1A subunit of the PP2A nucleic acid comprises at least one mutation (e.g., a substitution mutation at the P179 (e.g., P179R) or S256 (e.g., S256F)).

In certain embodiments, the invention provides a method of identifying an individual with an increased likelihood of having a condition associated with aberrant function of the PPP2R1A subunit of the PP2A protein (e.g., high grade subtypes of uterine cancer), comprising: (a) evaluating a sample containing nucleic acids from the individual for the presence or absence of one or more mutations in the PPP2R1A subunit of the PP2A gene (e.g., a substitution mutation at the P179 (e.g., P179R) or S256 (e.g., S256F)); and (b) identifying the individual as having an increased likelihood of having such a condition when one of such mutations is present in at least one allele.

The sample may be any suitable biological sample including, for example, whole blood, plasma, serum, and tissue samples (e.g., biopsy and paraffin-embedded tissue). In some embodiments, the biological sample is a uterine cancer tumor biopsy. In some embodiments, the biological sample is a high grade uterine cancer tumor biopsy (e.g., USC, UCC and UCS). The PPP2R1A subunit of the PP2A nucleic acid may be any convenient nucleic acid type including, for example, genomic DNA, RNA (e.g., mRNA), or cDNA prepared from subject RNA.

Alternatively, the PPP2R1A subunit of the PP2A nucleic acid mutation may be inferred by assessing the PPP2R1A subunit of the PP2A protein (encoded by the PP2A gene) from the individual. For example, identification of a mutant PPP2R1A subunit of the PP2A protein is indicative of a mutation in the PPP2R1A subunit of the PP2A gene. Suitable detection methodologies include oligonucleotide probe hybridization, primer extension reaction, nucleic acid sequencing, and protein sequencing.

The invention also provided oligonucleotides (e.g., primers and probes) suitable for assessing PPP2R1A subunit of the PP2A nucleic acid mutations. For example, suitable probes are designed to specifically hybridize to a nucleotide sequence containing at least one PPP2R1A subunit of the PP2A mutation disclosed herein (i.e., but not hybridize to a non-mutated sequence). Suitable primers include allele-specific primers and primers suitable for primer extension reactions (e.g., SNaPShot® primers). The invention also provides antibodies that specifically bind to mutated PPP2R1A subunit of the PP2A proteins encoded by the mutated PPP2R1A subunit of the PP2A nucleic acids disclosed herein.

In some embodiments, evaluating comprises using antibodies against wild type PPP2R1A subunit of the PP2A protein and each of the protein mutations encoded by mutations within the PPP2R1A subunit of the PP2A gene (e.g., a substitution mutation at the P179 (e.g., P179R) or S256 (e.g., S256F)). In another embodiment, evaluating comprises using protein sequencing.

In an embodiment of any of the foregoing aspects, "subject" and/or "patient" and/or "individual" refers to a human (e.g., a human being screened for a condition associated with aberrant function of the PPP2R1A subunit of the PP2A protein (e.g., high grade subtypes of uterine cancer)) (e.g., a human at risk for developing a condition associated with aberrant function of the PPP2R1A subunit of the PP2A protein (e.g., high grade subtypes of uterine cancer)).

In an embodiment of any of the foregoing aspects, the methods and uses further comprise the step of treating the subject having one or more mutations in the PPP2R1A subunit of the PP2A gene (e.g., a substitution mutation at the P179 (e.g., P179R) or S256 (e.g., S256F)) for a condition associated with aberrant function of the PPP2R1A subunit of the PP2A protein. In some embodiments, the condition associated with aberrant function of the PPP2R1A subunit of the PP2A protein is any type of cancer associated with aberrant function of the PPP2R1A subunit of the PP2A protein. In some embodiments, the condition is uterine cancer. In some embodiments, the condition is a high-grade uterine cancer (e.g., USC, UCC, UCS).

In some embodiments, the treatment is capable of mimicking wild-type function/activity of the PPP2R1A subunit of the PP2A protein. In some embodiments, the treatment is any pharmaceutical agent capable of mimicking wild-type function/activity of the PPP2R1A subunit of the PP2A protein (e.g., small molecule, a polypeptide or peptide fragment, an siRNA, or an antibody or fragment thereof). In some embodiments, the treatment is a DNA Damage Response Pathway (DDR) modulating agent.

In some embodiments, the DDR modulating agent is a ribonucleotide reductase inhibitor (e.g., clofarabine, cladribine). The term "ribonucleotide reductase inhibitors" refers to pyrimidine or purine nucleoside analogs including, but not limited to, fludarabine and/or cytosine arabinoside (ara-C), 6-thioguanine, 5-fluorouracil, clofarabine, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

In some embodiments, the DDR modulating agent is a poly ADP ribose polymerase (PARP) inhibitor. In some embodiments, the PARP inhibitor is selected from olaparib, rucaparib, or niraparib.

In some embodiments, the DDR modulating agent is a CDK1 inhibitor. In some embodiments, the CDK1 inhibitor is selected from SCH 727965, NU6027 and RO-3306.

In some embodiments, the DDR modulating agent is a CDCl$_7$ inhibitor. In some embodiments, the CDCl$_7$ inhibitor is PHA-767491.

In some embodiments, the treating comprises radiation therapy.

In some embodiments, the treating comprises chemotherapy (e.g., alkylating agents, antimetabolites, vinca alkaloids, etc.).

Additional embodiments will be apparent to persons skilled in the relevant art based on the teachings contained herein.

BRIEF DESCRIPTION OF THE DRAWINGS

FIG. 1A-N. High throughput screening identifies PP2A Aα mutations sensitize cancer cells to RNR inhibitors. A, Representative western blot of UT42$^{A\alpha-P179R}$ isogenic cells expressing EGFP or WT Aα protein demonstrating overexpression. B, Schematic of the high-throughput screening workflow. C, Overview of the viability results from all 3,200 compounds, with the viability of the EGFP expressing cells on the x-axis and the viability of the WT Aα protein expressing cells on the y-axis. Compounds included in the screen which are classified to harbor activity for ribonucleotide reductase from the high throughput screen were highlighted in red. D&E, Dose response curves of UT42 isogenic cells treated with Cladribine (D) or Clofarabine (E) as measured by MTT, n=3 biological replicates, error bars±SD. F, Calculated EC$_{50}$ values from the MTT assays in D and E (calculated from the average of all biological replicates). G-I, Isogenic UT42$^{A\alpha-P179R}$ (G), OV17R$^{A\alpha-S256F}$ (H) or UT89 CRISPR Aα-KO cells (I) were treated with Clofarabine and representative immunoblots of the apoptotic marker Cleaved Caspase 3 is shown, n=3 biological replicates. Quantification from the immunoblots shown is represented in Supplemental FIG. 3. J, Representative immunoblot of apoptotic markers Cleaved Caspase 3, Cleaved PARP, or RRM1 and RRM2 in isogenic UT42$^{A\alpha-P179R}$ cells with knockdown of RRM1, RRM2, or RLUC (Control) at 72 hrs., n=3 biological replicates. K&L, Dose response curves of UT42 isogenic cells treated with Nelarabine (K) or Cisplatin (L) as measured by MTT, n=3 biological replicates, error bars±SD. M&N, Calculated EC$_{50}$ values from the MTT assays in K and L (calculated from the average of all biological replicates).

FIG. 2A-G: PP2A Aα mutant cells are more sensitive to ribonucleotide reductase inhibitors. A, Overview of the data plotted for all 3,200 compounds, comprised of the Selleck Bioactives and Sigma LOPAC libraries. B, Common endometrial and ovarian standard of care compounds highlighted in blue. C, Dose response curves in UT42 isogenic cells treated with increasing doses of the RNR inhibitor Triapine at 72 hrs., n=3 biological replicates, error bars±SD. D, Dose response curves in UT42 isogenic cells treated with increasing doses of the RNR inhibitor Gemcitabine at 72 hrs., n=3 biological replicates, error bars±SD. E, Dose response curves in UT42 isogenic cells treated with increasing doses of the RNR inhibitor Hydroxyurea at 72 hrs., n=3 biological replicates, error bars±SD. F, Dose response curves in OV17R isogenic cells treated with increasing doses of Cisplatin at 72 hrs., n=3 biological replicates, error bars±SD. G, Dose response curves in OV17R isogenic cells treated with increasing doses of Nelarabine at 72 hrs., n=3 biological replicates, error bars±SD.

FIG. 4A-F: Characterization of additional PP2A Aα mutant cell models. A, Schematic of the generation of OV17R$^{256F}$ isogenic cell line model with a representative western blot of overexpression, n=3 biological replicates. B, Schematic of the generation of UT89$^{A\alpha-KO}$ isogenic cell line model with a representative western blot of overexpression, n=3 biological replicates. C, Quantification of A subunit expression levels from (B). No significant differences in A subunit level were detected in the Aα WT, Aα-P179R or Aα-S256F overexpressing cell lines, n=3 biological replicates. D-F, Quantification of cleaved caspase 3 levels, corresponding to FIG. 1 G-I, n=3 biological replicates, error bars±SD (one way ANOVA relative to EGFP+Clofarabine (C and D) or WT+Clofarabine (E) p-values: *<0.05, ****<0.0001).

FIG. 6A-K: PP2A Aα mutant tumors are sensitive to Clofarabine in vivo. A, Subcutaneous xenograft growth of control UT42$^{A\alpha-P179R}$ tumors treated with vehicle (solid line) or 30 mpk Clofarabine (dashed line), error bars±SEM, (multiple T-tests, p-values: ***<0.001). B, Subcutaneous xenograft growth of control OV89$^{A\alpha-KO}$ tumors expressing Aα-S256F treated with vehicle (solid line) or 30 mpk Clofarabine (dashed line), error bars±SEM, (multiple T-tests, p-values: *<0.05). C, Subcutaneous xenograft growth of control OV89$^{A\alpha-KO}$ tumors expressing Aα-P179R treated with vehicle (solid line) or 30 mpk Clofarabine (dashed line), error bars±SEM, (multiple T-tests, p-values: *<0.05). D, Waterfall plot of UT42$^{A\alpha-P179R}$ tumors treated with Control or Clofarabine showing the percent change in tumor volume, corresponding to (A). E, Waterfall plot of OV89$^{A\alpha-KO}$ tumors expressing Aα-S256F tumors treated with Control or Clofarabine showing the percent change in tumor volume, corresponding to (B). F, Waterfall plot of OV89$^{A\alpha-KO}$ tumors expressing Aα-P179R tumors treated with Control or Clofarabine showing the percent change in tumor volume, corresponding to (C). G, Schematic of the in vivo pharmacodynamic (PD) study. H, Quantification of the tumor volumes in the Control (n=6) and Clofarabine (n=6) treatment groups, indicating no difference in tumor volume at the imitation of the PD study. I, Lysates from Control and Clofarabine treated UT42$^{A\alpha-P179R}$ PD xenograft tumors were analyzed by western blot for gH2AX and Rad51, with Vinculin as a housekeeping protein. J and K, Quantification of gH2AX levels (J) and Rad51 (K) all tumors normalized relative to the average of the two control tumors. Error bars±SD, (Students T-test, p-values *<0.05).

FIG. 7A-G: Protein expression analysis of DNA damage and PP2A subunit proteins in Clofarabine treated terminal efficacy xenograft studies. A, Lysates from Control (n=9) and Clofarabine (n=9) treated UT89$^{A\alpha-KO+P179R}$ xenograft tumors were analyzed by western blot for gH2AX and total PP2A C Subunit, with Vinculin as a housekeeping protein. B, Quantification of gH2AX levels in (A), all tumors normalized to the average of two control tumors. Quantification of Total C Subunit levels in (FIG. 4). Error bars±SD, (Students T-test, p-values *<0.05). C, Lysates from Control (n=9) and Clofarabine (n=8) treated UT89$^{Aa-KO+S256F}$ xenograft tumors were analyzed by western blot for gH2AX and total PP2A C Subunit, with Vinculin as a housekeeping protein. Sample highlighted with an arrow was excluded due to insufficient protein concentration at lysis. D, Quantification of gH2AX levels in (C), all tumors normalized to the average of two control tumors. Quantification of Total C Subunit levels in (FIG. 4). Error bars±SD, (Students T-test, p-values ***, <0.001). E, Lysates from Control (n=9) and Clofarabine (n=9) treated UT42$^{Aa-P179R}$ xenograft tumors were analyzed by western blot for gH2AX and total PP2A C Subunit, with Vinculin as a housekeeping protein. Samples were run on three individual blots, as indicated, with two consistent control samples (1&2) on each blot for normalization. F, Quantification of gH2AX levels in (E), all tumors normalized to the average of the two indicated control tumors. Error bars±SD, (Students T-test, p-values *<0.05). G, Lysates from Control and Clofarabine treated UT42$^{Aa-P179R}$ PD xenograft tumors were analyzed by western blot for total C Subunit, with Vinculin as a housekeeping protein. Total C was probed on the same western blot as FIG. 4I, so the image for Vinculin is the same as the main figure.

FIG. 8A-H: Aα mutations impair checkpoint signaling and checkpoint control leading to increased accumulation of DNA damage following Clofarabine treatment. A Representative immunofluorescence images of γH2AX, DAPI, and Actin in isogenic UT42$^{Aa-P179R}$ cells treated with DMSO control (top) or 1 µM Clofarabine (bottom) for 3 hrs., n=3 biological replicates B, Representative immunofluorescence images of γH2AX, DAPI, and Actin in isogenic OV17R$^{Aa-S256F}$ cells treated with DMSO control (top) or 1 µM Clofarabine (bottom) for 3 hrs., n=3 biological replicates Representative western blots of UT42 isogenic cells treated with Clofarabine (1 µM) for 3 hrs. (left) and 6 hrs. (right), for checkpoint response proteins, n=3 biological replicates. C and D, Quantification of immunofluorescence images of UT42$^{Aa-P179R}$ isogenic cells (A) and OV17R$^{AaS256F}$ isogenic cells (B), n=3 biological replicates, error bars±SD, (One-way ANOVA relative to EGFP Clofarabine with Dunnett's correction for multiple comparisons, p-values , <0.01, **<0.0001). E and F, Quantification of γH2AX levels by immunoblot of UT42$^{Aa-P179R}$ isogenic cells (e) and OV17R$^{AaS256F}$ isogenic cells (f), n=3 biological replicates, error bars±SD, (One-way ANOVA relative to EGFP Clofarabine with Dunnett's correction for multiple comparisons, p-values *<0.05). G and H, Representative immunoblot of γH2AX in isogenic UT42$^{Aa-P179R}$ (G) and OV17R$^{AaS256F}$ (H), treated with 1 µM Clofarabine for 3 hrs., n=3 biological replicates, quantification in (E and F).

FIG. 9A-L: PP2A mutations impair checkpoint signaling induced by Clofarabine treatment. A, Representative western blots of UT42 isogenic cells treated with Clofarabine (1 µM) for 3 hrs. (left) and 6 hrs. (right), for checkpoint response proteins, n=3 biological replicates. B-E, Quantification of immunoblots in (A), n=3 biological replicates, error bars±SD, (One-way ANOVA relative to EGFP Clofarabine with Dunnett's correction for multiple comparisons, p-values *<0.05, ***, <0.001). F, Legend for graphs in B-E. G, Representative western blots of OV17R isogenic cells treated with Clofarabine (1 µM) for 3 hrs. (left) and 6 hrs. (right), for checkpoint response proteins, n=3 biological replicates. H-K, Quantification of immunoblots in (G), n=3 biological replicates, error bars±SD, (One-way ANOVA relative to EGFP Clofarabine with Dunnett's correction for multiple comparisons, p-values *<0.05, ***<0.001). L, Legend for graphs in H-K.

FIG. 10A-L: PP2A inactivation is common in serous uterine carcinomas and predicts sensitivity and response to Gemcitabine treatment in a cohort of patients. A, Analysis of heterozygous and homozygous loss of canonical PP2A subunits in uterine serous carcinoma samples from the TCGA. Subunits with loss at greater than 50% are highlighted in red. In aggregate, 101 of 109 USC patients harbor some alteration to PP2A. B and C, Dose response curve for UT42$^{Aa-P179R}$ cells expressing WT Aa (B) or OV-17R$^{Aa-S256F}$ cells expressing WT Aa (C) were treated with Clofarabine with or without LB-100 in increasing doses held at a constant ratio, n=3 biological replicates, error bars±SD. D, Quantification of total C Subunit levels in UT-89$^{Aa-KO+P179R}$ terminal efficacy xenograft tumors. All tumors normalized to the average of two control tumors. Error bars±SD, (Students T-test, p-values ***<0.001). E, Quantification of total C Subunit levels in UT89$^{Aa-KO+S256F}$ terminal efficacy xenograft tumors. All tumors normalized to the average of two control tumors. Error bars±SD, (Students T-test, p-values *<0.05). F, Quantification of total C Subunit levels in UT42$^{Aa-P179R}$ terminal efficacy xenograft tumors. All tumors normalized to the average of two control tumors. Error bars±SD, (Students T-test, p-values *<0.001). G, Quantification of total C Subunit levels in UT42$^{Aa-P179R}$ pharmacodynamic xenograft tumors from FIG. 2G. All tumors normalized to the average of two control tumors. Error bars±SD, (Students T-test, p-values *<0.001). Westerns for (D-E) can be found in Supplemental FIG. 5. H-J, Kaplan-Meier estimates of survival as stratified by histology. Blue line represents endometrioid or mixed endometrioid (not serous) histology, red line represents serous or mixed serous histology. (D) Overall survival of patients with recurrent disease from the TCGA (E) Time to next treatment following initiation of gemcitabine. (C) Initiation of gemcitabine to date of death or last follow-up. K, CT images of the first patient before initiation of gemcitabine (left) and after (right). L, CT images of the second patient before the initiation of gemcitabine (left) and after (right).

FIG. 13: Most PP2A alterations in USC are mutually exclusive. From the TCGA Uterine Serous Carcinoma dataset, pairwise comparisons were made for all 15 genes listed in FIG. 4A. Of the 105 comparisons made, only 15 were significant for co-occurrence (14.2%), listed above.

FIG. 14A-B: Inhibition of PP2A through LB-100 treatment is synergistic with Clofarabine in PP2A wild type USC cells. A and B, Calculated CompuSyn analysis of dose ratios from FIGS. 4B and C (F), with values<1 indicating synergy.

DETAILED DESCRIPTION OF THE INVENTION

Figure 2A:
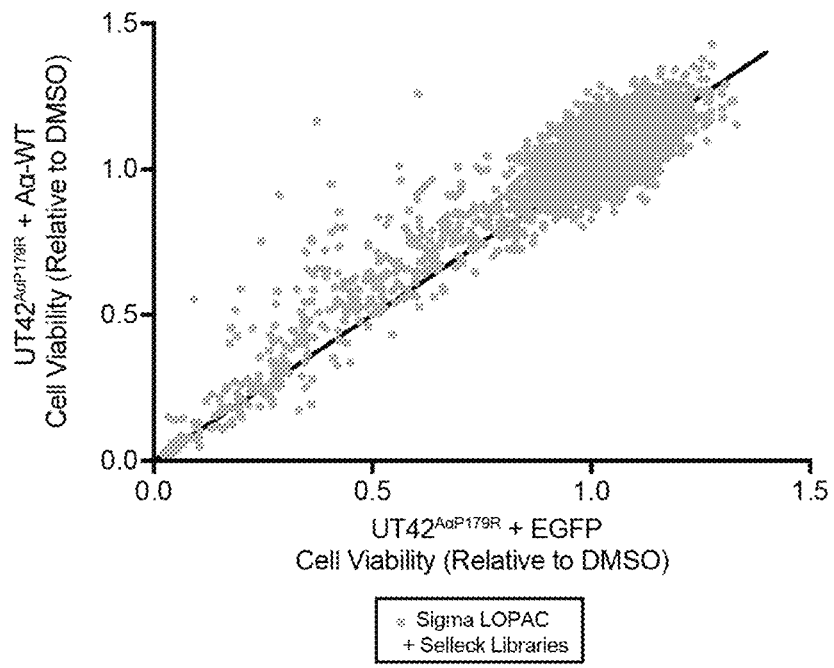
Figure 2B:
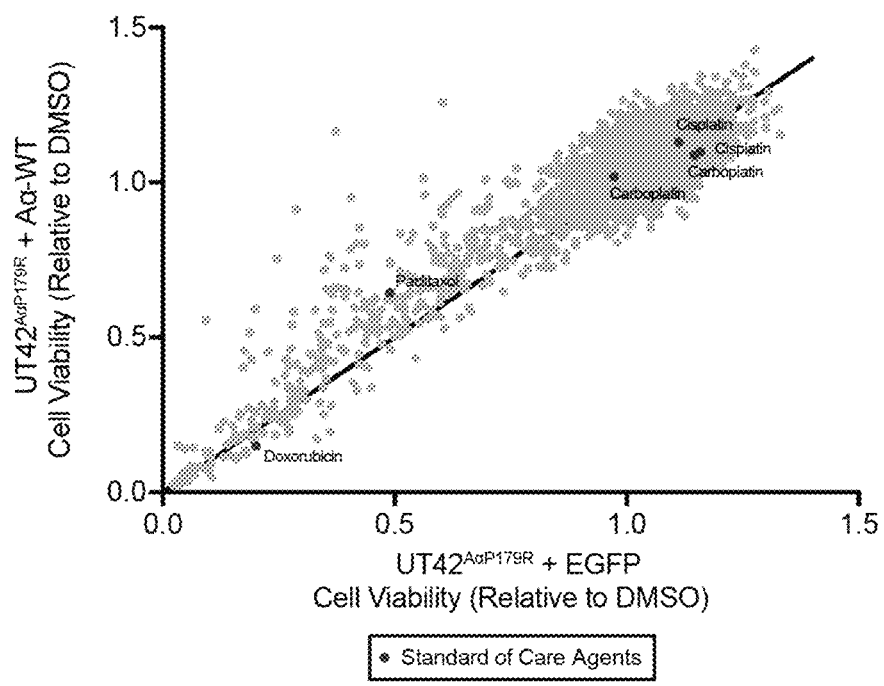

Currently, a lack of established drivers of the high-grade subtypes of uterine cancer (e.g., uterine serous carcinoma (USC), uterine clear cell carcinoma (UCC) and uterine carcinosarcoma (UCS)), has limited the use of targeted treatment strategies. Large-scale genomic profiling efforts have made progress in determining potential drivers of USC. First, it has been identified that p53 mutations are a hallmark of these tumors, present in 80-90% of all cases of USC. In addition, mutation to PPP2R1A, the scaffolding subunit of the tumor suppressor protein phosphatase 2A, have been found in 30-40% of USC patients (see, Gibson, W. J., et al., (2016) Nat Genet 48, 848-855; Kandoth, C., et al., (2013) Nature 497, 67-73). The most recurrently mutated sites in PPP2R1A in USC are P179 (e.g., P179R) and S256 (e.g., S256F), within a mutational hotspot region. Interestingly, this residue is uniquely mutated in gynecological malignancies, including high grade serous ovarian cancer, but is enriched in USC.

Protein phosphatase 2A (PP2A) is a key tumor suppressor responsible for the dephosphorylation of many oncogenic signaling pathways. The PP2A holoenzyme is comprised of a scaffolding subunit (Aα), which serves as the structural platform for the catalytic subunit (C) and for an array of regulatory subunits (Bs) to assemble. PP2A is a heterotrimeric family of phosphatases which functions as a tumor suppressor in cancer. As shown in FIG. 1, the A and C subunit make up the core dimer of the enzyme. This dimer will then bind one regulatory subunit, which guides PP2A's substrate specificity. The regulatory subunits exist in 4 families, and each family is made up of different isoforms, all encoded by different genes. The structural complexity of PP2A allows the enzyme to have over 60 different holoenzymes, which can be active in a cell at given time. These holoenzymes regulate multiple cellular processes through the dephosphorylation of their substrates. In cancer, PP2A is inactivated through a variety of mechanism including somatic mutation of the Aα subunit.

Experiments conducted during the course of developing embodiments for the present invention determined that mutation to Aα results in synthetic lethality to treatment with inhibitors of ribonucleotide reductase (RNR), and multiple models of Aa mutant uterine serous tumors were sensitive to Clofarabine, an RNR inhibitor in vivo. Aa mutant cells displayed impaired checkpoint signaling upon RNRi treatment, and subsequently accumulated more DNA damage than wild type cells. This was PP2A dependent as complete inhibition of PP2A activity using LB-100, a catalytic site inhibitor, sensitized wild type USC cells to RNRi. Finally, there was a trend for improved outcomes in USC patients treated with RNRi gemcitabine compared to patients with endometrioid histology. Overall, our data provide experimental evidence to support the use of ribonucleotide reductase inhibitors for the treatment of USC.

Accordingly, the present invention relates to methods and biomarkers for detection and characterization of conditions associated with aberrant function of the PPP2R1A subunit of the PP2A protein (e.g., high grade subtypes of uterine cancer) in biological samples (e.g., tissue samples, blood samples, plasma samples, cell samples, serum samples), and related methods of treatment. In particular, the present invention provides compositions and methods for characterizing a patient as having such a condition by identifying mutations in the PPP2R1A subunit of the PP2A gene or gene products, and related methods of treatment through administering to such a patient a DNA Damage Response Pathway (DDR) modulating agent (e.g., a ribonucleotide reductase inhibitor).

The present invention is based on the identification of mutations in the PPP2R1A subunit of the PP2A gene in patients diagnosed with high grade subtypes of uterine cancer (e.g., USC, UCC and UCS). The mutations include, but are not limited to, a substitution mutation at the P179 (e.g., P179R) or S256F in the PPP2R1A subunit of the PP2A gene. Accordingly, the invention also provides variant nucleic acids with these gene mutations and the resulting mutated proteins, methods and reagents for the detection of the variants disclosed herein, uses of these variants for the development of detection reagents, and assays or kits that utilize such reagents.

Such mutations within the PPP2R1A subunit of the PP2A gene may be assessed by any suitable method including, for example, by nucleic acid sequencing or oligonucleotide hybridization. For example, such mutations may be assessed by amplifying a target sequence of a PPP2R1A subunit of the PP2A nucleic acid (e.g., genomic DNA, RNA, or cDNA) containing all or a portion of the mutation. Relatedly, detection may involve using probes and/or primers capable of specifically hybridizing to the mutation site. Target sequences (including primer and probe sequences encompassing this mutation) may be of any suitable length (e.g., 20, 25, 30, 35, 40, 50, 100, 200, 300, or more nucleotides in length).

Alternatively, such mutations within the PPP2R1A subunit of the PP2A gene may be assessed by evaluating the PPP2R1A subunit of the PP2A protein (encoded by PP2A gene) present in a patient sample such as by specifically detecting a protein variant. PPP2R1A subunit of the PP2A protein assessment may be performed by any appropriate method including amino acid sequencing or through the use of mutant PP2A-specific antibodies (e.g., using an ELISA). Mutant PP2A proteins may be assessed by amino acid sequencing of all or a portion of the PPP2R1A subunit of the PP2A protein comprising the amino acid sequence encoded by one or more PPP2R1A subunit of the PP2A nucleic acid mutations (e.g., a substitution mutation at the P179 (e.g., P179R) or S256 (e.g., S256F) in the PPP2R1A subunit of the PP2A gene). Optionally, antibodies (polyclonal or monoclonal) can be raised against the polypeptide epitope having the amino acid sequence encoded by one or more of such PP2A gene mutations.

The methods and compositions of this invention may be used to detect mutations in the PPP2R1A subunit of the PP2A gene using a biological sample obtained from an individual. The nucleic acid (DNA or RNA) may be isolated from the sample according to any methods well known to those of skill in the art. Examples include tissue samples or any cell-containing or acellular bodily fluid. Biological samples may be obtained by standard procedures and may be used immediately or stored, under conditions appropriate for the type of biological sample, for later use.

Methods of obtaining test samples are well known to those of skill in the art and include, but are not limited to, aspirations, tissue sections, drawing of blood or other fluids, surgical or needle biopsies, and the like. The test sample may be obtained from an individual or patient diagnosed as having a high grade uterine cancer (e.g., USC, UCC and UCS). The test sample may be a cell-containing liquid or a tissue. Samples may include, but are not limited to, amniotic fluid, biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Samples may also be processed, such as sectioning of tissues, fractionation, purification, or cellular organelle separation.

If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the individual's cells to detect using polymerase chain reaction.

Methods of plasma and serum preparation are well known in the art. Either "fresh" blood plasma or serum, or frozen (stored) and subsequently thawed plasma or serum may be used. Frozen (stored) plasma or serum should optimally be maintained at storage conditions of −20 to −70° C. until thawed and used. "Fresh" plasma or serum should be refrigerated or maintained on ice until used, with nucleic acid (e.g., RNA, DNA or total nucleic acid) extraction being performed as soon as possible.

Blood can be drawn by standard methods into a collection tube, typically siliconized glass, either without anticoagulant for preparation of serum, or with EDTA, sodium citrate, heparin, or similar anticoagulants for preparation of plasma. A requirement for preparing plasma or serum for storage, although not an absolute requirement, is that plasma or serum is first fractionated from whole blood prior to being frozen. This reduces the burden of extraneous intracellular RNA released from lysis of frozen and thawed cells which might reduce the sensitivity of the amplification assay or interfere with the amplification assay through release of inhibitors to PCR such as porphyrins and hematin. "Fresh" plasma or serum may be fractionated from whole blood by centrifugation, using gentle centrifugation at 300-800 times gravity for five to ten minutes, or fractionated by other standard methods. High centrifugation rates capable of fractionating out apoptotic bodies should be avoided. Since heparin may interfere with RT-PCR, use of heparinized blood may require pretreatment with heparanase, followed by removal of calcium prior to reverse transcription (see, e.g., Imai, H., et al., J. Virol. Methods 36:181-184, (1992)). Thus, EDTA is a suitable anticoagulant for blood specimens in which PCR amplification is planned.

Variant PPP2R1A subunit of the PP2A nucleic acids or polypeptides (PPP2R1A subunit of the PP2A polypeptides) of the present invention may be detected as genomic DNA or mRNA using a variety of nucleic acid techniques known to those of ordinary skill in the art, including but not limited to: nucleic acid sequencing; nucleic acid hybridization; and, nucleic acid amplification.

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, fluorescent or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

Some embodiments of the present invention utilize next generation or high-throughput sequencing. A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323: 133-138 (2009); each of which is herein incorporated by reference in its entirety.

In some embodiments, sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (see, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKeman et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al.

(2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition.

Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, capillary electrophoresis (CE) is utilized to analyze amplification fragments. During capillary electrophoresis, nucleic acids (e.g., the products of a PCR reaction) are injected electrokinetically into capillaries filled with polymer. High voltage is applied so that the fluorescent DNA fragments are separated by size and are detected by a laser/camera system. In some embodiments, CE systems from Life Technogies (Grand Island, NY) are utilized for fragment sizing (see e.g., U.S. Pat. Nos. 6,706,162, 8,043,493, each of which is herein incorporated by reference in its entirety).

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, the present invention provides nucleic acid probes specific for a particular PPP2R1A subunit of the PP2A variant. For example, in some embodiments, separate nucleic acid probes are provided that are only specific for one PPP2R1A subunit of the PP2A variant as described herein (see, e.g., a substitution mutation at the P179 (e.g., P179R) or S256 (e.g., S256F) in the PPP2R1A subunit of the PP2A gene). In some embodiments, such separate nucleic acid probes specific for a PPP2R1A subunit of the PP2A variant will not bind the respective wild type equivalent. In some embodiments, such separate nucleic acid probes specific for a PPP2R1A subunit of the PP2A variant will not bind different PPP2R1A subunit of the PP2A variants.

In some embodiments, microarrays are utilized for detection of PPP2R1A subunit of the PP2A nucleic acid sequences and PPP2R1A subunit of the PP2A amino acid sequences. Examples of microarrays include, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Arrays can also be used to detect copy number variations at a specific locus. These genomic micorarrys detect microscopic deletions or other variants that lead to disease causing alleles.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

The nucleic acid to be amplified may be from a biological sample such as an organism, cell culture, tissue sample, and the like. The biological sample can be from a subject which includes any animal, preferably a mammal. A preferred subject is a human, which may be a patient presenting to a medical provider for diagnosis or treatment of a disease (e.g., a high grade subtype of uterine cancer). The volume of plasma or serum used in the extraction may be varied dependent upon clinical intent, but volumes of 100 μL to one milliliter of plasma or serum are usually sufficient.

Various methods of extraction are suitable for isolating the DNA or RNA. Suitable methods include phenol and chloroform extraction (see, e.g., Maniatis et al., Molecular Cloning, A Laboratory Manual, 2d, Cold Spring Harbor Laboratory Press, page 16.54 (1989)). Numerous commercial kits also yield suitable DNA and RNA including, but not limited to, QIAamp™ mini blood kit, Agencourt Genfind™, Roche Cobas® Roche MagNA Pure® or phenol:chloroform extraction using Eppendorf Phase Lock Gels®, and the NucliSens extraction kit (Biomerieux, Marcy l'Etoile, France). In other methods, mRNA may be extracted from patient blood/bone marrow samples using MagNA Pure LC mRNA HS kit and Mag NA Pure LC Instrument (Roche Diagnostics Corporation, Roche Applied Science, Indianapolis, Ind.).

Nucleic acid extracted from tissues, cells, plasma or serum can be amplified using nucleic acid amplification techniques well known in the art. Many of these amplification methods can also be used to detect the presence of mutations simply by designing oligonucleotide primers or probes to interact with or hybridize to a particular target sequence in a specific manner. By way of example, but not by way of limitation, these techniques can include the polymerase chain reaction (PCR), reverse transcriptase polymerase chain reaction (RT-PCR), nested PCR, ligase chain reaction (see, e.g., Abravaya, K., et al., Nucleic Acids Research, 23:675-682, (1995)), branched DNA signal amplification (see, e.g., Urdea, M. S., et al., AIDS, 7 (suppl 2):S11-S14, (1993)), amplifiable RNA reporters, Q-beta replication, transcription-based amplification, boomerang DNA amplification, strand displacement activation, cycling probe technology, isothermal nucleic acid sequence based amplification (NASBA) (see, e.g., Kievits, T. et al., J Virological Methods, 35:273-286, (1991)), Invader Technology, or other sequence replication assays or signal amplification assays. These methods of amplification each described briefly below and are well-known in the art.

Some methods employ reverse transcription of RNA to cDNA. As noted, the method of reverse transcription and amplification may be performed by previously published or recommended procedures, which referenced publications are incorporated herein by reference in their entirety. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus Thermophilus*. For example, one method, but not the only method, which may be used to convert RNA extracted from plasma or serum to cDNA is the protocol adapted from the Superscript II Preamplification system (Life Technologies, GIBCO BRL, Gaithersburg, Md.; catalog no. 18089-011) (see, e.g., Rashtchian, A., PCR Methods Applic., 4:S83-S91, (1994)).

PCR is a technique for making many copies of a specific template DNA sequence. The reaction consists of multiple amplification cycles and is initiated using a pair of primer sequences that hybridize to the 5' and 3' ends of the sequence to be copied. The amplification cycle includes an initial denaturation, and typically up to 50 cycles of annealing, strand elongation and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al., J of Clin Micro, 33(3):556-561 (1995). Briefly, a PCR reaction mixture includes two specific primers, dNTPs, approximately 0.25 U of Taq polymerase, and 1×PCR Buffer.

LCR is a method of DNA amplification similar to PCR, except that it uses four primers instead of two and uses the enzyme ligase to ligate or join two segments of DNA. LCR can be performed as according to Moore et al., J Clin Micro, 36(4):1028-1031 (1998). Briefly, an LCR reaction mixture contains two pair of primers, dNTP, DNA ligase and DNA polymerase representing about 90 μl, to which is added 100 μl of isolated nucleic acid from the target organism. Amplification is performed in a thermal cycler (e.g., LCx of Abbott Labs, Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., PNAS, 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 minutes for the synthesis of RNA. The above steps are then repeated. Alternatively, after the initial cDNA synthesis, both RT and RNA polymerase are added following a 1 minute 100° C. denaturation followed by an RNA elongation of approximately 30 minutes at 37° C. TAS can be also be performed on solid phase as according to Wylie et al., J Clin Micro, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µA TMA reaction mixture is placed in a tube, 200 µA oil reagent is added and amplification is accomplished by incubation at 42° C. in a waterbath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian myeloblastosis virus (AMV) reverse transcriptase, RNase H and T7 RNA polymerase are used. This method can be performed as according to Heim, et al., Nucleic Acids Res., 26(9):2250-2251 (1998). Briefly, an NASBA reaction mixture contains two specific primers, dNTP, NTP, 6.4 U of AMV reverse transcriptase, 0.08 U of *Escherichia coli* Rnase H, and 32 U of T7 RNA polymerase. The amplification is carried out for 120 min at 41° C. in a total volume of 20 µl.

In a related method, self-sustained sequence-replication (3SR) reaction, isothermal amplification of target DNA or RNA sequences in vitro using three enzymatic activities: reverse transcriptase, DNA-dependent RNA polymerase and *Escherichia coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager Eur J Biochem, 235:256-261, 1996).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., PNAS, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo-Klenow polymerase). The sample mixture is heated 95° C. for 4 minutes to denature target DNA prior to addition of the enzymes. After addition of the two enzymes, amplification is carried out for 120 min. at 37° C. in a total volume of 50 µl. Then, the reaction is terminated by heating for 2 min. at 95° C.

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi Trends Biotechnol. 1991 9(2):53-8, 1991).

A variety of amplification enzymes are well known in the art and include, for example, DNA polymerase, RNA polymerase, reverse transcriptase, Q-beta replicase, thermostable DNA and RNA polymerases. Because these and other amplification reactions are catalyzed by enzymes, in a single step assay the nucleic acid releasing reagents and the detection reagents should not be potential inhibitors of amplification enzymes if the ultimate detection is to be amplification based. Amplification methods suitable for use with the present methods include, for example, strand displacement amplification, rolling circle amplification, primer extension preamplification, or degenerate oligonucleotide PCR (DOP). These methods of amplification are well known in the art and each described briefly below.

In suitable embodiments, PCR is used to amplify a target or marker sequence of interest. The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity.

For analyzing mutations and other variant nucleic acids, it may be appropriate to use oligonucleotides specific for alternative alleles. Such oligonucleotides which detect single nucleotide variations in target sequences may be referred to by such terms as "allele-specific probes", or "allele-specific primers". The design and use of allele-specific probes for analyzing polymorphisms is described in, e.g., Mutation Detection A Practical Approach, ed. Cotton et al. Oxford University Press, 1998; Saiki et al., Nature, 324:163-166 (1986); Dattagupta, EP235,726; and Saiki, WO 89/11548. In one embodiment, a probe or primer may be designed to hybridize to a segment of target DNA such that the SNP aligns with either the 5' most end or the 3' most end of the probe or primer.

In some embodiments, the amplification may include a labeled primer, thereby allowing detection of the amplification product of that primer. In particular embodiments, the amplification may include a multiplicity of labeled primers; typically, such primers are distinguishably labeled, allowing the simultaneous detection of multiple amplification products.

In one type of PCR-based assay, an allele-specific primer hybridizes to a region on a target nucleic acid molecule that overlaps a SNP position and only primes amplification of an allelic form to which the primer exhibits perfect complementarity (Gibbs, 1989, Nucleic Acid Res., 17:2427-2448). Typically, the primer's 3'-most nucleotide is aligned with and complementary to the SNP position of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target mutation position) because this position is most destabilizing to elongation from the primer (see, e.g., WO 93/22456).

In a specific embodiment, a primer contains a sequence substantially complementary to a segment of a target mutation-containing nucleic acid molecule except that the primer has a mismatched nucleotide in one of the three nucleotide positions at the 3'-most end of the primer, such that the mismatched nucleotide does not base pair with a particular allele at the mutation site. In one embodiment, the mismatched nucleotide in the primer is the second from the last nucleotide at the 3'-most position of the primer. In another embodiment, the mismatched nucleotide in the primer is the last nucleotide at the 3'-most position of the primer.

In one embodiment, primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

The present invention also contemplates reagents that do not contain (or that are complementary to) a mutated nucleotide sequence identified herein but that are used to assay one or more of the mutations disclosed herein. For example, primers that flank, but do not hybridize directly to a target position provided herein are useful in primer extension reactions in which the primers hybridize to a region adjacent to the target position (i.e., within one or more nucleotides from the target mutation site). During the primer extension reaction, a primer is typically not able to extend past a target mutation site if a particular nucleotide (allele) is present at that target site, and the primer extension product can readily be detected in order to determine which allele (i.e., wildtype or mutant) is present. For example, particular ddNTPs are typically used in the primer extension reaction to terminate primer extension once a ddNTP is incorporated into the extension product. Thus, reagents that bind to a nucleic acid molecule in a region adjacent to a mutation site, even though the bound sequences do not necessarily include the mutation site itself, are also encompassed by the present invention.

Variant nucleic acids may be amplified prior to detection or may be detected directly during an amplification step (i.e., "real-time" methods). In some embodiments, the target sequence is amplified and the resulting amplicon is detected by electrophoresis. In some embodiments, the specific mutation or variant is detected by sequencing the amplified nucleic acid. In some embodiments, the target sequence is amplified using a labeled primer such that the resulting amplicon is detectably labeled. In some embodiments, the primer is fluorescently labeled.

In one embodiment, detection of a variant nucleic acid is performed using the TaqMan® assay, which is also known as the 5' nuclease assay (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, PCR Method Appl., 4:357-362; Tyagi et al, 1996, Nature Biotechnology, 14:303-308; Nazarenko et al., 1997, Nucl. Acids Res., 25:2516-2521; U.S. Pat. Nos. 5,866,336 and 6,117,635). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

TaqMan® primer and probe sequences can readily be determined using the variant and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the variants of the present invention are useful in diagnostic assays for neurodevelopmental disorders and related pathologies, and can be readily incorporated into a kit format. The present invention also includes modifications of the TaqMan® assay well known in the art such as the use of Molecular Beacon probes (U.S. Pat. Nos. 5,118,801 and 5,312,728) and other variant formats (U.S. Pat. Nos. 5,866,336 and 6,117,635).

In an illustrative embodiment, real time PCR is performed using TaqMan® probes in combination with a suitable amplification/analyzer such as the ABI Prism® 7900HT Sequence Detection System. The ABI PRISM® 7900HT Sequence Detection System is a high-throughput real-time PCR system that detects and quantitates nucleic acid sequences. Briefly, TaqMan® probes specific for the amplified target or marker sequence are included in the PCR amplification reaction. These probes contain a reporter dye at the 5' end and a quencher dye at the 3' end. Probes hybridizing to different target or marker sequences are conjugated with a different fluorescent reporter dye. During PCR, the fluorescently labeled probes bind specifically to their respective target or marker sequences; the 5' nuclease activity of Taq polymerase cleaves the reporter dye from the probe and a fluorescent signal is generated. The increase in fluorescence signal is detected only if the target or marker sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation. Real time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually.

Other methods of probe hybridization detected in real time can be used for detecting amplification a target or marker sequence flanking a tandem repeat region. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target or marker sequence, the probe is unfolded, the quencher is moved from the fluorophore, and the resultant fluorescence can be detected.

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. Amplified fragments may be detected using standard gel electrophoresis methods. For example, in preferred embodiments, amplified fractions are separated on an agarose gel and stained with ethidium bromide by methods known in the art to detect amplified fragments.

Another suitable detection methodology involves the design and use of bipartite primer/probe combinations such as Scorpion™ probes. These probes perform sequence-specific priming and PCR product detection is achieved using a single molecule. Scorpion™ probes comprise a 3' primer with a 5' extended probe tail comprising a hairpin structure which possesses a fluorophore/quencher pair. The probe tail is "protected" from replication in the 5' to 3' direction by the inclusion of hexethlyene glycol (HEG) which blocks the polymerase from replicating the probe. The fluorophore is attached to the 5' end and is quenched by a moiety coupled to the 3' end. After extension of the Scorpion™ primer, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion™, resulting in an extension product. A fluorescent signal is generated due to the separation of the fluorophore from the quencher resulting from the binding of the probe element of the Scorpion™ to the extension product. Such probes are described in Whitcombe et al., Nature Biotech 17: 804-807 (1999).

In other embodiments, variant PPP2R1A subunit of the PP2A polypeptides (encoded by the PPP2R1A subunit of the PP2A gene) are detected. Any suitable method may be used to detect truncated or mutant PPP2R1A subunit of the PP2A polypeptides. For example, detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

PPP2R1A subunit of the PP2A proteins (encoded by the PPP2R1A subunit of the PP2A gene) with and without insertion/truncation mutation may be recovered from biological sample from an individual, culture medium or from host cell lysates. If membrane-bound, it can be released from the membrane using a suitable detergent solution (e.g., Triton-X 100) or by enzymatic cleavage. Cells employed in the expression of PPP2R1A subunit of the PP2A protein can be disrupted by various physical or chemical means, such as freeze-thaw cycling, sonication, mechanical disruption, or cell lysing agents.

It may be desired to purify PPP2R1A subunit of the PP2A protein from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the BCR-ABL. Various methods of protein purification may be employed and such methods are known in the art and described for example in Deutscher, Methods in Enzymology (1990), 182:83-89; Scopes, Protein Purification: Principles and Practice, Springer-Verlag, New York (1982). The purification step(s) selected will depend, for example, on the nature of the production process, source of PPP2R1A subunit of the PP2A used and the particular PPP2R1A subunit of the PP2A produced.

Several methods for detection of proteins are well known in the art. Detection of the proteins could be by resolution of the proteins by SDS polyacrylamide gel electrophoresis (SDS PAGE), followed by staining the proteins with suitable stain for example, Coomassie Blue. The PPP2R1A proteins with and without a mutation (encoded by the PP2A gene) can be differentiated from each other and also from other proteins by Western blot analysis using mutation-specific antibodies. Methods of Western blot are well known in the art and described for example in W. Burnette W. N. Anal. Biochem. 1981; 112 (2): 195-203.

Alternatively, flow cytometry may be applied to detect the mutant and wildtype PPP2R1A protein. Antibodies specific for either the mutant or wildtype protein can be coupled to beads and can be used in the flow cytometry analysis.

In some embodiments, protein microarrays may be applied to identify the various PPP2R1A protein variants. Methods of protein arrays are well known in the art. In one example, antibodies specific for each protein may be immobilized on the solid surface such as glass or nylon membrane. The proteins can then be immobilized on the solid surface through the binding of the specific antibodies. Antibodies may be applied that bind specifically to a second epitope (e.g., an epitope common to the mutant and wildtype) of the PPP2R1A proteins. The first antibody/protein/second antibody complex can then be detected using a detectably labeled secondary antibody. The detectable label can be detected as discussed for polynucleotides.

Various procedures known in the art may be used for the production of antibodies to epitopes of the PPP2R1A protein that may be used to distinguish among the protein variants. Such antibodies include but are not limited to polyclonal, monoclonal, chimeric, single chain, Fab fragments and fragments produced by a Fab expression library.

Antibodies may be radioactively labeled allowing one to follow their location and distribution in the body after injection. Radioactivity tagged antibodies may be used as a non-invasive diagnostic tool for imaging de novo cells of tumors and metastases.

Immunotoxins may also be designed which target cytotoxic agents to specific sites in the body. For example, high affinity PPP2R1A-specific monoclonal antibodies may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate mutant PPP2R1A protein-expressing cells.

For the production of antibodies, various host animals may be immunized by injection with the full length or fragment of PPP2R1A proteins including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum.*

Monoclonal antibodies to PPP2R1A proteins may be prepared by using any technique which provides for the production of antibody molecules by continuous cell lines in culture. These include but are not limited to the hybridoma technique originally described by Kohler and Milstein, (Nature (1975), 256:495-497), the human B-cell hybridoma technique (Kosbor et al., Immunology Today (1983), 4:72; Cote et al. Proc. Natl. Acad. Sci. (1983), 80:2026-2030) and the EBV-hybridoma technique (Cole et al., Monoclonal Antibodies and Cancer Therapy (1985), Alan R. Liss, Inc., pp. 77-96). In addition, techniques developed for the production of "chimeric antibodies" (Morrison et al., Proc. Natl. Acad. Sci. USA (1984), 81:6851-6855; Neuberger et al., Nature (1984), 312:604-608; Takeda et al., Nature (1985), 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce PPP2R1A protein-specific single chain antibodies.

Antibody fragments may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., Science. 1989; 246: 1275-1281) to allow rapid and easy identification of monoclonal Fab fragments with the desired specificity.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology for detecting a specific PPP2R1A variant described herein (e.g., a PPP2R1A variant encoded by one of the PPP2R1A subunit of the PP2A mutations described herein) combines mass spectrometry with immunoassay. First, a biospecific capture reagent (e.g., an antibody, aptamer or Affibody that recognizes the biomarker and other forms of it) is used to capture the biomarker of interest (e.g., a PPP2R1A variant). Preferably, the biospecific capture reagent is bound to a solid phase, such as a bead, a plate, a membrane or an array. After unbound materials are washed away, the captured analytes are detected and/or measured by mass spectrometry. In some embodiments, such methods also permit capture of protein interactors, if present, that are bound to the proteins or that are otherwise recognized by antibodies and that, themselves, can be biomarkers. Various forms of mass spectrometry are useful for detecting the protein forms, including laser desorption approaches, such as traditional MALDI or SELDI, and electrospray ionization.

In some embodiments, a biomarker of this invention (e.g., a PPP2R1A variant encoded by one of the PPP2R1A subunit of the PP2A mutations described herein) is detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In some embodiments, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

In some embodiments, the mass spectrometric technique for use is "Surface Enhanced Laser Desorption and Ionization" or "SELDI," as described, for example, in U.S. Pat. Nos. 5,719,060 and 6,225,047; each herein incorporated by reference in its entirety. This refers to a method of desorption/ionization gas phase ion spectrometry (e.g. mass spectrometry) in which an analyte (e.g., one or more of the biomarkers of the present invention) is captured on the surface of a SELDI mass spectrometry probe. There are several versions of SELDI.

One version of SELDI is called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047; herein incorporated by reference in its entirety. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and LSAX-30 (anion exchange); WCX-2, CM-10 and LWCX-30 (cation exchange); IMAC-3, MAC-30 and IMAC 40 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities that adsorb transition metal ions, such as copper, nickel, zinc, and gallium, by chelation. Preactivated ProteinChip arrays have acyl-imidizole or epoxide functional groups that can react with groups on proteins for covalent binding. Such biochips are further described in: U.S. Pat. Nos. 7,045,366, 6,579,719; 6,897,072; 6,555,813; U.S. Patent Publication Nos. U.S. 2003-0032043; US 2003-0218130; and PCT International Publication No. WO 03/040700; each herein incorporated by reference in its entirety.

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Another version of SELDI is Surface-Enhanced Neat Desorption (SEND), which involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyanohydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate "C18 SEND"). SEND is further described in U.S. Pat. No. 6,124,137 and PCT International Publication No. WO 03/64594; each herein incorporated in its entirety.

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

In some embodiments, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. For example, in some embodiments, the present invention provides biochips having attached thereon one or more capture reagents specific for a MAP2K1 variant of the present invention.

Protein biochips are biochips adapted for the capture of polypeptides (e.g., a PPP2R1A variant encoded by one of PPP2R1A subunit of PP2A mutations described herein). Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. Nos. 6,225,047, 6,537,749, 6,329,209, and 5,242,828, and PCT International Publication Nos. WO 00/56934, and WO 03/048768; each herein incorporated by reference in its entirety.

In certain embodiments, the present invention provides methods for managing a subject's treatment based on the status (e.g., presence or absence of a high grade subtype of uterine cancer). Such management includes the actions of the physician or clinician subsequent to determining status. For example, if a physician makes a diagnosis of a high grade subtype of uterine cancer, then a certain regime of treatment, such as prescription or administration of therapeutic agent might follow. Alternatively, a diagnosis of non-mature form might be followed with further testing to determine a specific disease that the patient might be suffering from. Also, if the diagnostic test gives an inconclusive result on status, further tests may be called for.

In another aspect, the present invention provides compositions of matter based on the biomarkers of this invention. For example, in one embodiment, the present invention provides a biomarker of this invention in purified form. Purified biomarkers have utility as antigens to raise antibodies. Purified biomarkers also have utility as standards in assay procedures. As used herein, a "purified biomarker" is a biomarker that has been isolated from other proteins and peptides, and/or other material from the biological sample in which the biomarker is found. For example, in some embodiments, the present invention provides compositions comprising a purified PPP2R1A variant (e.g., a PPP2R1A variant encoded by one of the PP2A mutations described herein).

Biomarkers may be purified using any method known in the art, including, but not limited to, mechanical separation (e.g., centrifugation), ammonium sulphate precipitation, dialysis (including size-exclusion dialysis), size-exclusion chromatography, affinity chromatography, anion-exchange chromatography, cation-exchange chromatography, and methal-chelate chromatography. Such methods may be performed at any appropriate scale, for example, in a chromatography column, or on a biochip.

In another embodiment, the present invention provides a biospecific capture reagent, optionally in purified form, that specifically binds a biomarker of this invention. In one embodiment, the biospecific capture reagent is an antibody. Such compositions are useful for detecting the biomarker in a detection assay, e.g., for diagnostics.

In another embodiment, this invention provides an article comprising a biospecific capture reagent that binds a biomarker of this invention, wherein the reagent is bound to a solid phase. For example, this invention contemplates a device comprising bead, chip, membrane, monolith or microtiter plate derivatized with the biospecific capture reagent. Such articles are useful in biomarker detection assays.

In another aspect the present invention provides a composition comprising a biospecific capture reagent, such as an antibody, bound to a biomarker of this invention, the composition optionally being in purified form. Such compositions are useful for purifying the biomarker or in assays for detecting the biomarker.

In another embodiment, this invention provides an article comprising a solid substrate to which is attached an adsorbent, e.g., a chromatographic adsorbent or a biospecific capture reagent, to which is further bound a biomarker of this invention.

In another embodiment, the invention provides compositions comprising reaction mixtures formed through, for example, binding of a biomarker of the present invention with a detection marker (e.g., antibody, proble, biochip, etc.) (e.g., via a detection assay of the present invention). In some embodiments, "reaction mixture" comprises any material sufficient, necessary, or useful for conducting any of the assays described herein. In some embodiments, the present invention provides compositions comprising reaction mixtures comprising extension products complementary to a specific mutation. In some embodiments, the present invention provides compositions comprising reaction mixtures comprising extension products complementary to a specific mutation and sequences immediately surrounding such a mutation. In some embodiments, the extension product has thereon an labeling agent (e.g., a fluorophore or other lable). In some embodiments, the present invention provides compositions comprising reaction mixtures comprising extension products complementary to a specific mutation bound with such a complementary sequence. In some embodiments, the present invention provides compositions comprising reaction mixtures comprising extension products complementary to a specific mutation bound with such a complementary sequence, wherein the binding is to a solid surface, a biochip (e.g., in single copy or multiple copies). In some embodiments, the present invention provides compositions comprising fragments of a peptide of interest. In some embodiments, the present invention provides compositions comprising a peptide of interest in a mass-spectrometry compatible buffer.

In some embodiments, a computer-based analysis program is used to translate raw data generated by detection assay (e.g., the presence, absence, or amount of a given PPP2R1A subunit of PP2A related allele or PPP2R1A polypeptide) of the present invention into data of predictive value for a clinician. The clinician can access the predictive data using any suitable means. Thus, in some preferred embodiments, the present invention provides the further benefit that the clinician, who may not be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a blood or serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant PPP2R1A subunit of PP2A related allele or PPP2R1A protein), specific for the screening, diagnostic or prognostic information desired for the subject.

The profile data is then prepared in a format suitable for interpretation by a treating clinician. For example, rather than providing raw data, the prepared format may represent a diagnosis or risk assessment (e.g., diagnosis or prognosis of a high grade subtype of uterine cancer) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

In some embodiments, the methods disclosed herein are useful in monitoring the treatment of a high grade subtype of uterine cancer. For example, in some embodiments, the methods may be performed immediately before, during and/or after a treatment to monitor treatment success. In some embodiments, the methods are performed at intervals on disease free patients to ensure treatment success.

The present invention also provides a variety of computer-related embodiments. Specifically, in some embodiments the invention provides computer programming for analyzing and comparing a pattern of uterine cancer-specific marker detection results in a sample obtained from a subject to, for example, a library of such marker patterns known to be indicative of the presence or absence of uterine cancer, or a particular stage or prognosis of uterine cancer.

In some embodiments, the present invention provides computer programming for analyzing and comparing a first and a second pattern of uterine cancer-specific marker detection results from a sample taken at least two different time points. In some embodiments, the first pattern may be indicative of a pre-cancerous condition and/or low risk condition for uterine cancer and/or progression from a pre-cancerous condition to a cancerous condition. In such embodiments, the comparing provides for monitoring of the progression of the condition from the first time point to the second time point.

In yet another embodiment, the invention provides computer programming for analyzing and comparing a pattern of uterine cancer-specific marker detection results from a sample to a library of uterine cancer-specific marker patterns known to be indicative of the presence or absence of uterine cancer, wherein the comparing provides, for example, a differential diagnosis between an aggressively malignant uterine cancer and a less aggressive uterine cancer (e.g., the marker pattern provides for staging and/or grading of the cancerous condition).

The methods and systems described herein can be implemented in numerous ways. In one embodiment, the methods involve use of a communications infrastructure, for example the internet. Several embodiments of the invention are discussed below. It is also to be understood that the present invention may be implemented in various forms of hardware, software, firmware, processors, distributed servers (e.g., as used in cloud computing) or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of gastrointestinal neoplasm-specific marker detection results from a sample). This information received can be stored at least temporarily in a database, and data analyzed in comparison to a library of marker patterns known to be indicative of the presence or absence of a pre-cancerous condition, or known to be indicative of a stage and/or grade of uterine cancer.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In some embodiments, all or a portion of the input data and/or all or a portion of the output data (e.g., usually at least the library of the pattern of uterine cancer-specific marker detection results known to be indicative of the presence or absence of a pre-cancerous condition) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where detected marker data for a sample obtained from a subject is to be input by a user (e.g., a technician or someone performing the assays)) and transmitted to a remote site to a second computer processor for analysis (e.g., where the pattern of uterine cancer-specific marker detection results is compared to a library of patterns known to be indicative of the presence or absence of a pre-cancerous condition), where the first and second computer processors are connected by a network, e.g., via an intranet or internet). The system can also include a user component(s) for input; and a reviewer component(s) for review of data, and generation of reports, including detection of a pre-cancerous condition, staging and/or grading of uterine cancer, or monitoring the progression of a pre-cancerous condition or uterine cancer. Additional components of the system can include a server component(s); and a database(s) for storing data (e.g., as in a database of report elements, e.g., a library of marker patterns known to be indicative of the presence or absence of a pre-cancerous condition and/or known to be indicative of a grade and/or a stage of uterine cancer, or a relational database (RDB) which can include data input by the user and data output. The computer processors can be processors that are typically found in personal desktop computers (e.g., IBM, Dell, Macintosh), portable computers, mainframes, minicomputers, tablet computer, smart phone, or other computing devices.

The input components can be complete, stand-alone personal computers offering a full range of power and features to run applications. The user component usually operates under any desired operating system and includes a communication element (e.g., a modem or other hardware for connecting to a network using a cellular phone network, Wi-Fi, Bluetooth, Ethernet, etc.), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe, or distributed across multiple servers (e.g., as in cloud computing applications) and offers data management, information sharing between clients, network administration and security. The application and any databases used can be on the same or different servers. Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

In certain embodiments, the present invention provides methods for obtaining a subject's risk profile for developing uterine cancer or having an aggressive form of uterine cancer. In some embodiments, such methods involve obtaining a blood or blood product sample from a subject (e.g., a human at risk for developing uterine cancer; a human undergoing a routine physical examination, or a human diagnosed with uterine cancer), detecting the presence or absence of PPP2R1A variants described herein in the sample, and generating a risk profile for developing uterine cancer or progressing to a metastatic or aggressive form of such uterine cancer. For example, in some embodiments, a generated profile will change depending upon specific markers and detected as present or absent or at defined threshold levels. The present invention is not limited to a particular manner of generating the risk profile. In some embodiments, a processor (e.g., computer) is used to generate such a risk profile. In some embodiments, the processor uses an algorithm (e.g., software) specific for interpreting the presence and absence of specific exfoliated epithelial markers as determined with the methods of the present invention. In some embodiments, the presence and absence of specific PPP2R1A variants described herein as determined with the methods of the present invention are imputed into such an algorithm, and the risk profile is reported based upon a comparison of such input with established norms (e.g., established norm for pre-cancerous condition, established norm for various risk levels for developing uterine cancer, established norm for subjects diagnosed with various stages of uterine cancer). In some embodiments, the risk profile indicates a subject's risk for developing uterine cancer or a subject's risk for re-developing uterine cancer. In some embodiments, the risk profile indicates a subject to be, for example, a very low, a low, a moderate, a high, and a very high chance of developing or re-developing uterine cancer or having a poor prognosis (e.g., likelihood of long term survival) from uterine cancer. In some embodiments, a health care provider (e.g., an oncologist) will use such a risk profile in determining a course of treatment or intervention (e.g., biopsy, wait and see, referral to an oncologist, referral to a surgeon, etc.).

The present inventions also contemplate diagnostic systems in kit form. A diagnostic system of the present inventions may include a kit which contains, in an amount sufficient for at least one assay, any of the hybridization assay probes, amplification primers, and/or antibodies against PPP2R1A subunit of PP2A wild type and mutant proteins in a packaging material. Typically, the kits will also include instructions recorded in a tangible form (e.g., contained on paper or an electronic medium) for using the packaged probes, primers, and/or antibodies in a detection assay for determining the presence or amount of variant mRNA or protein in a test sample.

The various components of the diagnostic systems may be provided in a variety of forms. For example, the required enzymes, the nucleotide triphosphates, the probes, primers, and/or antibodies may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present inventions may contain a reconstitution reagent for reconstituting the lyophilized reagents of the kit. In preferred kits, the enzymes, nucleotide triphosphates and required cofactors for the enzymes are provided as a single lyophilized reagent that, when reconstituted, forms a proper reagent for use in the present amplification methods.

Some preferred kits may further contain a solid support for anchoring a nucleic acid of interest (e.g., PPP2R1A subunit of the PP2A nucleic acid) on the solid support. The target nucleic acid may be anchored to the solid support directly or indirectly through a capture probe anchored to the solid support and capable of hybridizing to the nucleic acid of interest. Examples of such solid support include but are not limited to beads, microparticles (for example, gold and other nano particles), microarray, microwells, multiwell plates. The solid surfaces may comprise a first member of a binding pair and the capture probe or the target nucleic acid may comprise a second member of the binding pair. Binding of the binding pair members will anchor the capture probe or the target nucleic acid to the solid surface. Examples of such binding pairs include but are not limited to biotin/streptavidin, hormone/receptor, ligand/receptor, antigen/antibody.

In an embodiment of any of the foregoing aspects, the methods and uses further comprise the step of treating the subject having one or more mutations in the PPP2R1A subunit of the PP2A gene (e.g., a substitution mutation at the P179 (e.g., P179R) or S256 (e.g., S256F)) for a condition associated with aberrant function of the PPP2R1A subunit of the PP2A protein. In some embodiments, the condition associated with aberrant function of the PPP2R1A subunit of the PP2A protein is any type of cancer associated with aberrant function of the PPP2R1A subunit of the PP2A protein. In some embodiments, the condition is uterine cancer. In some embodiments, the condition is a high-grade uterine cancer (e.g., USC, UCC, UCS).

In some embodiments, the treatment is capable of mimicking wild-type function/activity of the PPP2R1A subunit of the PP2A protein. In some embodiments, the treatment is any pharmaceutical agent capable of mimicking wild-type function/activity of the PPP2R1A subunit of the PP2A protein (e.g., small molecule, a polypeptide or peptide fragment, an siRNA, or an antibody or fragment thereof). In some embodiments, the treatment is a DNA Damage Response Pathway (DDR) modulating agent.

In some embodiments, the DDR modulating agent is a ribonucleotide reductase inhibitor (e.g., clofarabine, cladribine). The term "ribonucleotide reductase inhibitors" refers to pyrimidine or purine nucleoside analogs including, but not limited to, fludarabine and/or cytosine arabinoside (ara-C), 6-thioguanine, 5-fluorouracil, clofarabine, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

In some embodiments, the DDR modulating agent is a poly ADP ribose polymerase (PARP) inhibitor. In some embodiments, the PARP inhibitor is selected from olaparib, rucaparib, or niraparib.

In some embodiments, the DDR modulating agent is a CDK1 inhibitor. In some embodiments, the CDK1 inhibitor is selected from SCH 727965, NU6027 and RO-3306.

In some embodiments, the DDR modulating agent is a $CDCl_7$ inhibitor. In some embodiments, the $CDCl_7$ inhibitor is PHA-767491.

In some embodiments, the treating comprises radiation therapy.

In some embodiments, the treating comprises chemotherapy (e.g., alkylating agents, antimetabolites, vinca alkaloids, etc.).

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

Figure 3A:
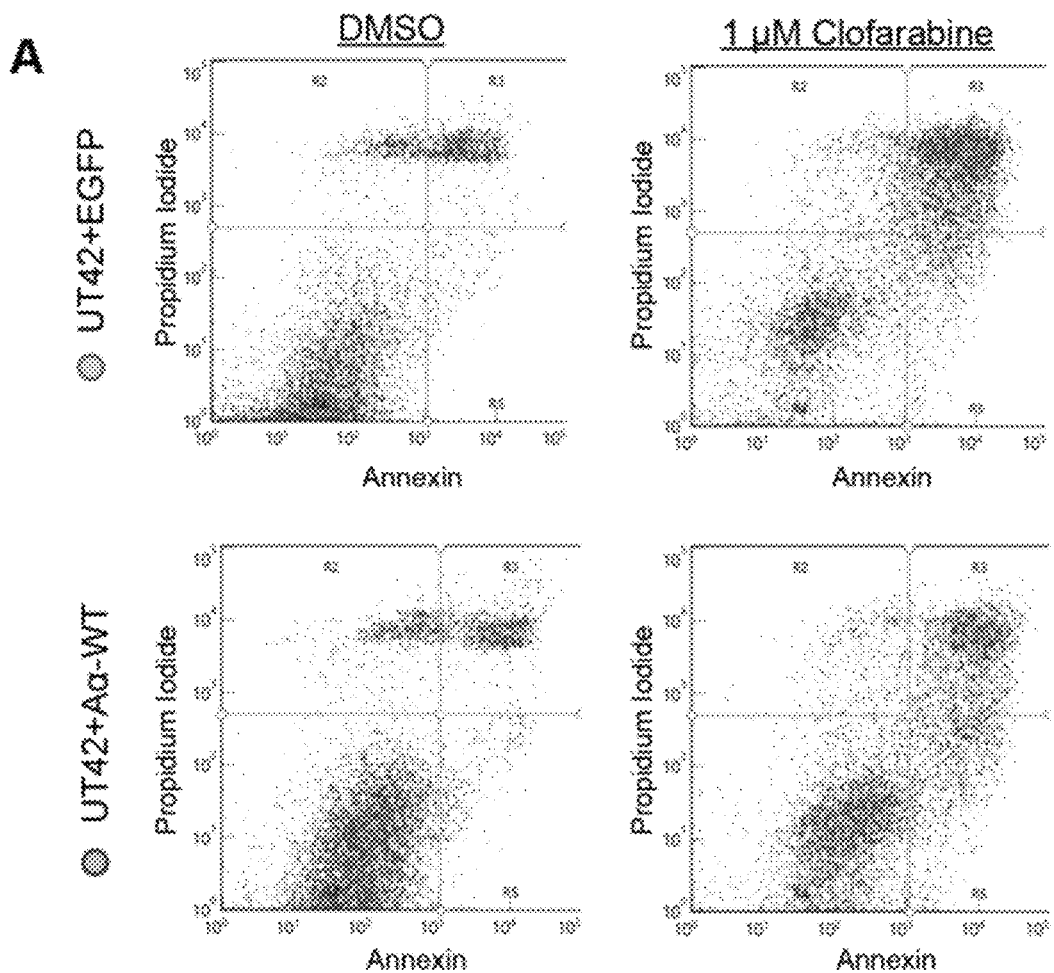
FIG. 3A-B: UT42 Aα mutant cells have more apoptosis in response to Clofarabine. A, Representative flow cytometry plots of mutant (EGFP, green) and wild type (purple) UT42 cells treated with 1 μM Clofarabine for 24 hours as measured by Annexin/PI staining, n=3 biological replicates. B, Quantification of n=3 biological replicates, error bars±SD, (one-way ANOVA relative to EGFP+Clofarabine, p-values **<0.01).
Figure 3B:
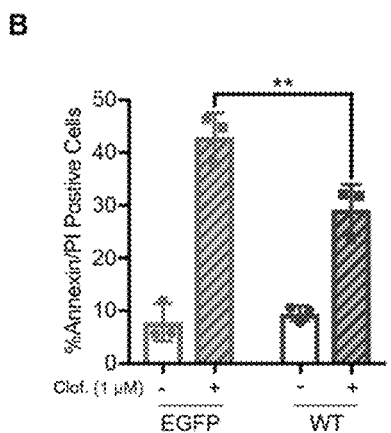

PP2A Aα-P179R Mutation Sensitizes Serous Endometrial Cancer Cells to RNR Inhibitors To evaluate the relevance of PP2A Aα P179R mutations to drug response, we (the inventors) used high-throughput screening (HTS) approach to test the drug sensitives and resistance of 3,200 bioactive compounds. We used a patient derived cellular model, UT42, which harbors a heterozygous Aα-P179R mutation ($UT42^{A\alpha-P179R}$), and compared viability changes of $UT42^{A\alpha-P179R}$ cells expressing EGFP (control) or wild type (WT) Aα (mutational correction), described previously (FIGS. 1A and B) (3). To compare viability changes between EGFP and Aα-WT expressing $UT42^{A\alpha-P179R}$ cells, the viability of +EGFP cells (mutant) were plotted on the x-axis and the viability of +Aα-WT cells were plotted on the y-axis, where each dot represents a different compound (FIG. 1C, FIGS. 2A and B, Table 1). Of particular interest were compounds falling above the line, indicating increased drug sensitivity in the Aα mutant expressing cells compared to the WT cells, which included the ribonucleotide reductase (RNR) inhibitor class of compounds, highlighted in red (FIG. 1C, Table 1). We performed dose response curves of multiple RNR inhibitors identified in the screen, including Cladribine, Clofarabine, Gemcitabine and Hydroxyurea, and independently confirmed the original screening results (FIG. 1D-F, FIG. 2C-E) (19,20). Due to the extensive difference in $EC_{50}$ with Clofarabine, and the ability to use an oral preparation for this compound in in vivo studies, we focused our future experiments on this RNR inhibitor. Apoptosis was measured by Annexin V/PI staining and similarly showed a higher percentage of apoptotic cells in the mutant cells compared to the Aα-WT expressing cells when treated with Clofarabine (FIGS. 3A & B).

TABLE 1

Summary of relevant viability results from high-throughput screening of isogenic $UT42^{AP179R}$ cells

| Compound | Mutant Viability | Wild Type Viability |
|---|---|---|
| RNR Inhibitors | | |
| Cladribine | 43% | 80% |
| Clofarabine | 25% | 75% |
| Fludarabine | 107% | 112% |

TABLE 1-continued

Summary of relevant viability results from high-throughput screening of isogenic UT42$^{AP179R}$ cells

| Compound | Mutant Viability | Wild Type Viability |
|---|---|---|
| Gemcitabine | 46%, 37% | 62%, 64% |
| Hydroxyurea | 102%, 107% | 115%, 120% |
| Triapine | 36% | 76% |
| DNA Incorporators and Nucleoside Analogues | | |
| 5-Azacytidine | 83% | 77% |
| 5-Fluorouracil | 103% | 111% |
| Azacitidine | 55% | 54% |
| Azaguanine-8 | 43% | 53% |
| Azathioprine | 49%, 49% | 53%, 55% |
| Carmofur | 103%, 104% | 103%, 118% |
| Cyclocitidine HCl | 61% | 77% |
| Cytarabine | 73% | 85% |
| Decitabine | 64% | 70% |
| Nelarabine | 107% | 117% |
| Penciclovir | 103% | 104% |

Clofarabine Treatment Results in Increased Apoptosis of P179R and S256F Mutant Cells To validate whether these recurrent scaffold mutations were driving the differential response to RNR inhibitors, we sought to correct these mutations using CRISPR/Cas9, but were unable to do so, likely as a result of low efficiency of homologous recombination and the dependency of this cell line on this mutation. Therefore, to expand our model systems and validate our results, we used two additional cell models (FIG. 4A-C). The first was OV17R cells, which harbor a heterozygous Aα-S256F mutation (OV-17R$^{Aα-S256F}$). OV17R$^{Aα-S256F}$ cells were stably transduced to express EGFP (control) or wild type Aα (mutational correction) (FIG. 4A). Additionally, we used UT89 cells, a patient derived serous endometrial cancer cell line which is wild type for PP2A Aα, and knocked out the Aα subunit, which we have described previously (UT89$^{AαKO}$) (3,21). UT89$^{AαKO}$ cells were transduced to stably express V5 tagged Aα-WT, Aα-P179R or Aα-S256F and the levels of the A subunit, C subunit and V5 was determined by western blot (FIGS. 4B and C).

All three cell models were treated with Clofarabine for 72 hours, and consistent with the cell viability assays, the mutant cells showed significantly more cleaved caspase 3, indicating higher amounts of apoptosis in the mutant cells upon Clofarabine treatment compared to the Aα-WT expressing cells (FIG. 1G-I and FIG. 4D-F).

Figure 5A:
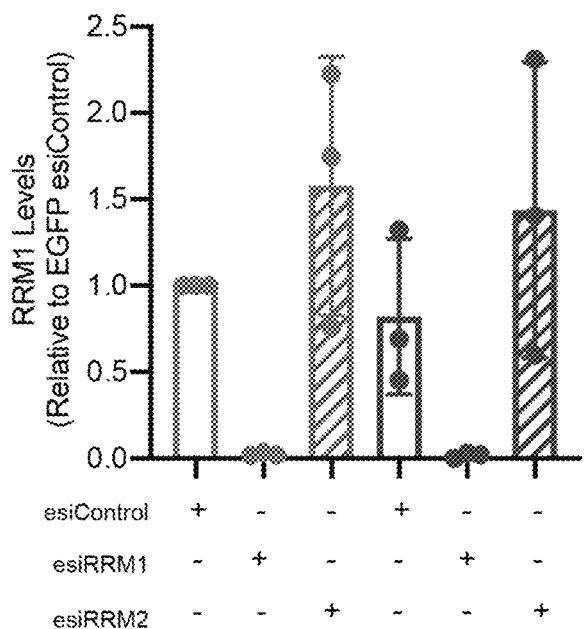
FIG. 5A-B: esiRNAs targeting RRM1 and RRM2 provide efficient knockdown. A, Quantification of RRM1 levels in UT42 isogenic cells treated with esiControl, esiRRMI1, or esiRRM2, n=3 biological replicates, error bars±SD. B, Quantification of RRM2 levels in UT42 isogenic cells treated with esiControl, esiRRMI1, or esiRRM2, n=3 biological replicates, error bars±SD.
Figure 5B:
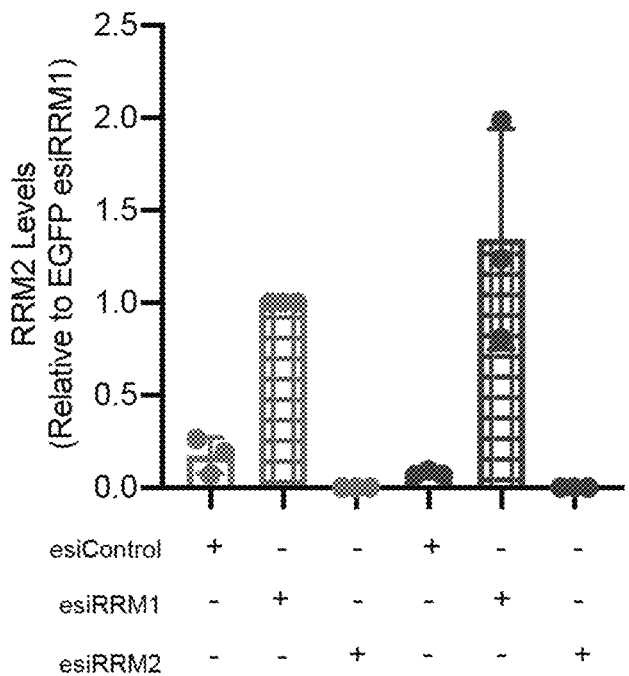

The Synthetic Lethality Between RNRi and PP2A is Dependent on Ribonucleotide Reductase We investigated whether the synthetic lethality was specific to RNR inhibition or also true for other nucleoside analogues or DNA damaging agents. First, we used pooled siRNAs to knock down the two main subunits of RNR, RRM1 and RRM2 in the isogenic UT42$^{Aα-P179R}$ cells and measured markers of apoptosis including cleaved PARP and cleaved caspase 3 following knockdown (FIG. 1J and FIGS. 5A and B). Consistent with the inhibitor data, siRNAs targeting RRM1 or RRM2 resulted in more apoptosis in the mutant Aα cells as compared to the wild type cells. Additionally, we treated the isogenic UT42 and OV17R cells with Nelarabine, a nucleoside analogue sharing high chemical similarity to Clofarabine or Cladribine but with minimal to no RNR inhibitory properties (FIGS. 1K and M, FIG. 2F) (22). These experiments showed no differences in viability between the mutant and wild type Aα cells, further indicating that the synthetic lethality is specific to RNR inhibition. Finally, treatment of WT and mutant cells with Cisplatin, a compound showing equal response in the HTS, showed equal response in a dose response curve, further supporting the screening results and specificity to RNR (FIGS. 1L and N, FIG. 2G).

Taken together, these data identified a potential synthetic lethal interaction between inhibition of ribonucleotide reductase in Aα mutant cells. Further analysis of additional cell models confirmed that the Aα-P179R cells are more sensitive to RNR inhibitors, in particular Clofarabine, and also show that this sensitivity profile is consistent in cells expressing other recurrent gynecological specific mutations, including Aα-S256F.

PP2A Aα Mutated Tumors are Sensitive to Clofarabine Treatment In Vivo

To determine if PP2A Aα mutant serous endometrial tumors were sensitive to Clofarabine treatment in vivo, we performed multiple independent xenograft studies. We have previously published a long latency period for UT-42$^{Aα-P179R}$ tumors (3). To limit the latency, we grew the cells subcutaneously in immunocompromised SRG rats, and subsequently sectioned and implanted tumor fragments into immunocompromised mice for treatment (23,24). These UT42$^{Aα-P179R}$ tumors were randomized and treated with 30 mg/kg Clofarabine or vehicle control once per day by oral gavage. Consistent with cell-based data, treatment of Clofarabine resulted in a significant tumor growth inhibition in this model (FIGS. 6A and D). Further, injected the UT89$^{Aα-KO}$ cells expressing mutant Aα-P179R or S256F subcutaneously into immunocompromised mice and tumors were subsequently randomized and treaded with vehicle control or 30 mg/kg Clofarabine once per day by oral gavage. In these xenograft studies, the mutant tumors also responded to Clofarabine treatment (FIGS. 6B and C, FIGS. 6E and F).

Ribonucleotide reductase inhibitors, including Clofarabine, result in a depletion of the dNTP pools necessary for DNA replication, leading to DNA damage (25). To evaluate whether treatment of Clofarabine was leading to an accumulation of DNA damage in vivo, we lysed tumor samples and analyzed for γH2AX, a marker of dsDNA breaks, by immunoblot. Paradoxically, analysis of the tumors for all three studies showed a significant reduction in γH2AX levels in all three in vivo studies (FIG. 7A-F), leading us to hypothesize that by the terminal endpoint the treated cells remaining in the tumor had become resistant to Clofarabine. To test this, we performed a pharmacodynamic xenograft study, where UT42$^{Aα-P179R}$ tumor fragments were implanted into immunocompromised mice, randomized when tumors reached 500 mm³, and treated with three doses of Clofarabine or vehicle control by oral gavage over three days (FIGS. 6G and H). Analysis of this study showed a significant increase in multiple DNA damage markers including γH2AX and Rad51, a marker of ssDNA breaks (FIG. 6I-K), further supporting the resistance acquired upon completion of the terminal efficacy studies as well as confirming Clofarabine activity at this dose in vivo.

Combined, these studies show that PP2A Aα mutant cells are sensitive to Clofarabine in vivo and tumors treated with Clofarabine result in an accumulation of DNA damage, highlighting the potential therapeutic benefit of using these compounds for the treatment of USC, a subtype of cancer with limited therapeutic options.

PP2A Aα Mutations Impair Checkpoint Signaling and Increase DNA Damage Upon Replication Stress Induced by Clofarabine Treatment Ribonucleotide reductase inhibitors impede the progression of replication forks and activates replication checkpoint kinases (25). To understand why PP2A Aα mutant cells were preferentially sensitive to Clofarabine treatment, we analyzed the phosphorylation and activation of checkpoint kinases in wild type PP2A Aα and mutant cells by western blot (FIG. 8A-F). Analysis of phosphorylated/total ratios of the checkpoint kinases ATR, CHK1, ATM, and CHK2 showed lower levels of activation in the mutant cells compared to the wild type cells in both the UT42$^{A\alpha\text{-}P179R}$ and OV17$^{A\alpha\text{-}S256F}$ cell models following 3 and 6 hours of Clofarabine treatment (FIG. 9A-L).

To determine if the impaired checkpoint signaling and control in the PP2A Aα mutant cells was in turn resulting in DNA damage, we analyzed γH2AX foci by immunofluorescent microscopy in both the UT42$^{A\alpha\text{-}P179R}$ and OV-17$^{A\alpha\text{-}S256F}$ cell models following Clofarabine treatment (FIG. 9A-D). This revealed an increase in the amount of accumulated dsDNA damage in the PP2A Aα mutant cells, consistent with a lack of checkpoint control. These findings were further confirmed by measuring γH2AX levels by western blot (FIG. 9E-H). Interestingly, these analyses also revealed increased γH2AX in both mutant cells at baseline, indicating a higher level of DNA damage in these cells in the absence of RNR inhibition.

Taken together, these data indicate that the inability of PP2A mutant cells to initiate the replication checkpoint results in an accumulation of dsDNA damage in response to the replicative stress induced by Clofarabine treatment both in vitro and in vivo.

Figure 11:
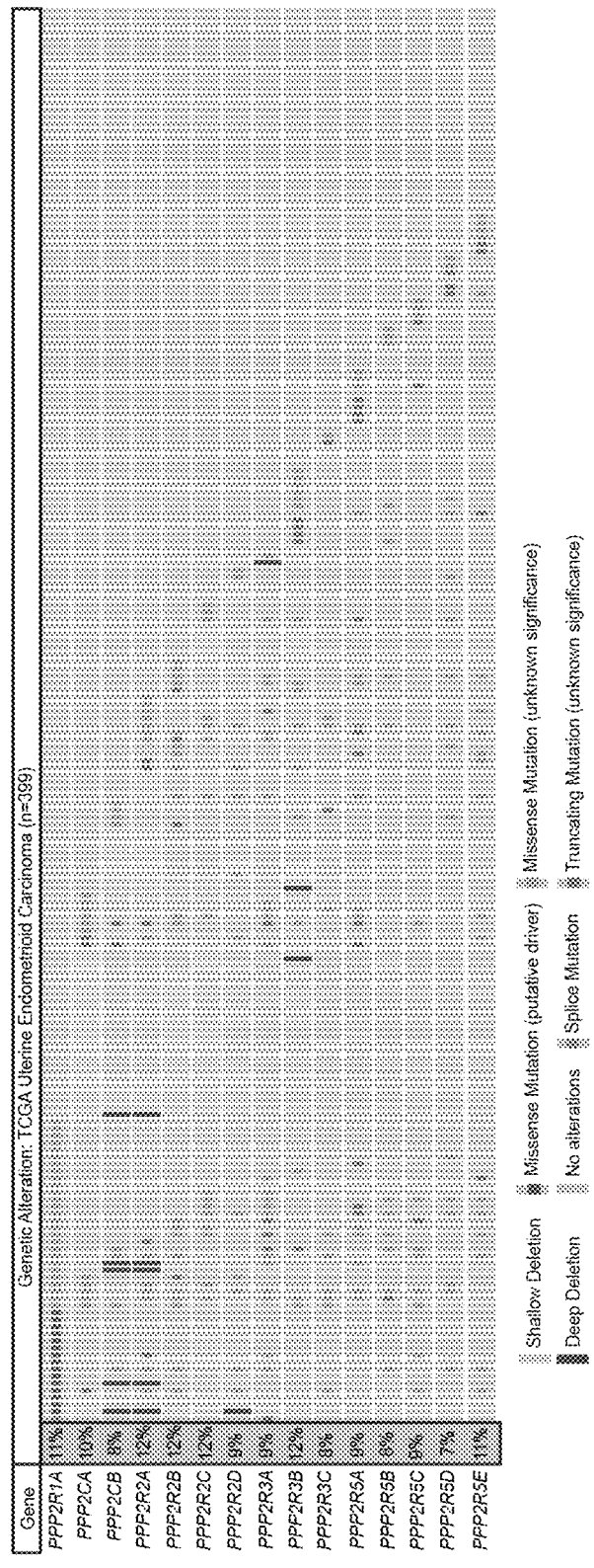
FIG. 11: PP2A is infrequently altered in Uterine Endometrioid Carcinomas. Shallow deletion (heterozygous loss), deep deletion (homozygous loss), and mutation of listed PP2A subunits from Uterine Endometrioid Carcinoma patients from the TCGA (n=399).
Figure 12:
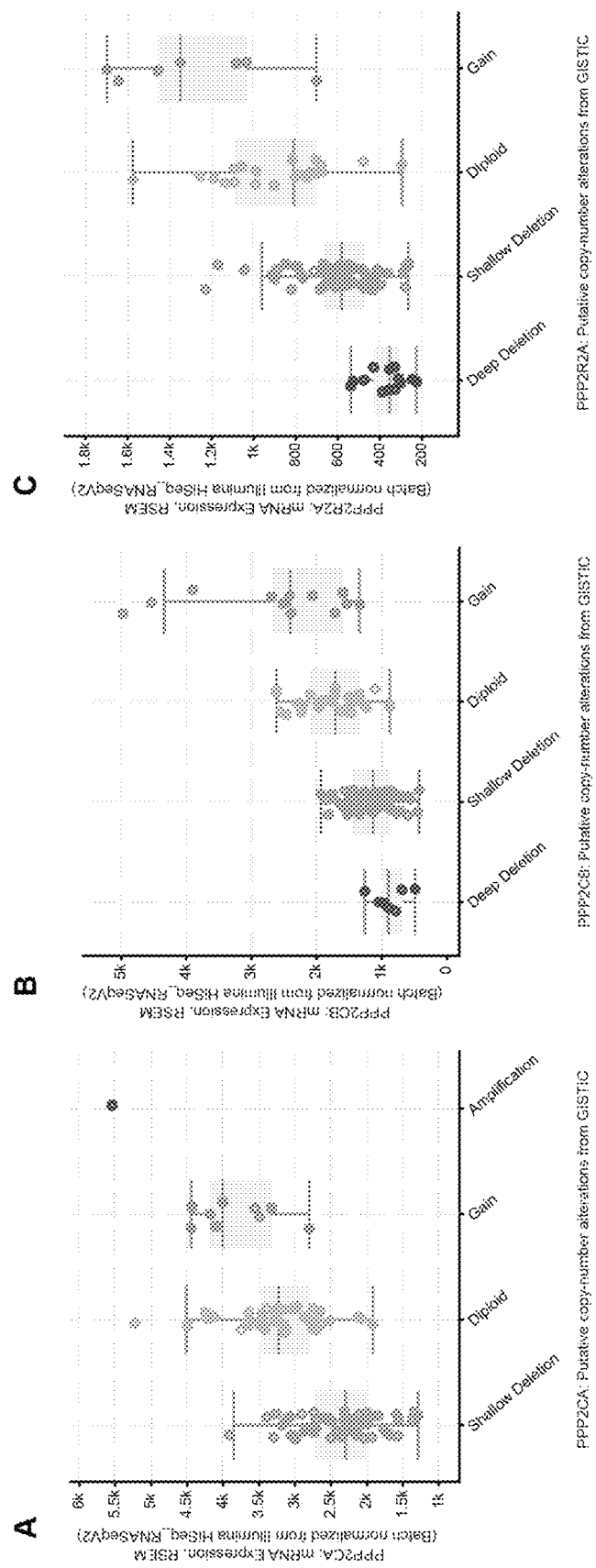
FIG. 12A-C: Copy Number Alterations from the TCGA correspond to mRNA levels. Copy number calls is plotted on the x-axis and mRNA expression is plotted on the y-axis from Uterine Serous Carcinoma patients (n=109) from the TCGA, for select PP2A genes PPP2CA (A), PPP2CB (B), and PPP2R2A (C).

Inhibition of PP2A is Common in USC and Mediates the Synthetic Lethality with Clofarabine Given the high prevalence and tumorigenic nature of Aα mutations in USC (2,3,5,6,26,27), we postulated that dysregulation or inactivation of PP2A might be a more widespread phenomenon in this highly aggressive uterine cancer subtype. To explore this, we analyzed the prevalence of expression loss of PP2A family genes, specifically within high-grade serous uterine cancer samples in The Cancer Genome Atlas (TCGA) and found that heterozygous loss of either catalytic subunit Cα/β (PPP2CA/B) or B55α (PPP2R2A) to be the most commonly lost PP2A subunit genes, at a rate ranging from 50-75%, (n=109) (FIG. 10A). Interestingly, analysis of endometrioid endometrial carcinomas did not share the same result, with very low frequencies of PP2A subunit loss or mutation (FIG. 11). This is consistent with the idea that PP2A inhibition through Aα mutation seem to be an early driver event for USC specifically (6,28). Importantly, further analysis of this data showed a correlation between mRNA and copy number, indicating that the heterozygous loss called by the TCGA did in fact correlate to decreased mRNA expression (FIG. 12). Testing for mutual exclusivity revealed that 88% of USC patients harbored at least one alteration in these genes (96/109), with a significant co-occurrence between loss of PPP2CB and PPP2R2A (FIG. 13). Our group and others have previously shown that mutations to the Aα subunit of PP2A cause structural defects resulting in the inability to form active PP2A heterotrimers, including loss of binding of the C subunit (3-5,17,21).

This data, combined with the highly prevalent loss of the PP2A C subunit isoforms, led us to hypothesize that loss of catalytic subunit expression may also be predictive marker of ribonucleotide reductase sensitivity, and the synthetic lethality identified here could occur in the majority of USC patients. To test this, we used LB-100, a catalytic site inhibitor of PP2A currently being used in clinical trials. Treatment with LB-100 in combination with Clofarabine showed synergy in both UT42$^{A\alpha\text{-}P179R}$ and OV17$^{A\alpha\text{-}S256F}$ cells expressing WT Aα, showing that the inhibition of PP2A's catalytic activity could phenocopy the effects of a mutant Aα, sensitizing cells to Clofarabine treatment (FIG. 10B-C, FIGS. 14A and B).

Finally, we were interested in exploring the expression levels of PP2A subunits in the control tumor samples and those treated with Clofarabine (FIG. 6). When PP2A C subunit levels were analyzed in these studies, we found that the Clofarabine treated samples in the terminal efficacy studies had significantly more PP2A C subunit expression than the vehicle control treated tumors, again suggestive of acquired resistance in these models (FIG. 10D-F, FIG. 7A-F). Additionally, this data supports the indication that PP2A activity, through increased C subunit expression, may be a resistance mechanism to RNRi, supportive of PP2A mediating synthetic lethality we identified RNR inhibitors. Finally, in contrast to the increase in PP2A C subunit levels in the terminal efficacy studies, analysis of the pharmacodynamic UT42$^{A\alpha\text{-}P179R}$ samples showed no changes in PP2A C subunit expression (FIG. 10G).

Together, this data suggests that PP2A is essential for a cells ability to respond to replicative stress. In the event of a PP2A scaffolding mutation, a common event in USC, the C subunit is unable to bind and is degraded (3,21). When these cells are then treated with Clofarabine or other ribonucleotide reductase inhibitors, they are unable to effectively activate the replicative checkpoint signals, accumulate DNA damage, and undergo cell death as a result. Further, impairment of PP2A's catalytic activity also render USC more sensitive to Clofarabine treatment, broadening the potential clinical and translational impact of these findings.

Uterine Serous Carcinomas are More Responsive to Gemcitabine than Uterine Endometrioid Carcinomas Given the prevalence of PP2A subunit loss in USC, we were interested in exploring if RNR inhibition could be a potential therapeutic strategy for this subtype of uterine cancer. The serous subtype of uterine carcinoma is highly aggressive, and the overall prognosis is typically worse in this subtype due to high risk of recurrence. To determine whether USCs also exhibit inferior prognosis in the setting of recurrent disease, patients with recurrent disease were selected from The Cancer Genome Atlas (TCGA) (29,30), and, when stratified by histology, 55 patients had endometrioid carcinoma and 31 patients had serous carcinoma. Overall survival (from time of diagnosis) of this study showed that overall survival of the endometrioid cohort was 38.1 months vs 31.4 months for the serous cohort, although this did not meet statistical significance likely due to small sample size (p=0.17) (FIG. 10H).

While RNR inhibitors are not routinely used for uterine cancers, we have identified a cohort of patients with recurrent disease treated with gemcitabine at MSKCC as a second or later line therapy. A total of 83 patients were identified from this unique patient cohort. Included patients were those with serous, endometrioid, or mixed endometrial adenocarcinoma histology that received gemcitabine as monotherapy or in combination with a platinum-based agent during the study period. Patients were excluded if they received less than two doses of gemcitabine, received gemcitabine for an unrelated malignancy, or had lack of adequate follow-up information. Prior to initiation of gemcitabine, the median number of prior lines of therapy was 3 (range 0-11) and 98% (n=81) received a prior platinum agent. When stratified by histology, 45 patients had serous or mixed adenocarcinoma with serous features and 38 patients had endometrioid or mixed adenocarcinoma without serous features. In the serous cohort, 38% (n=17) patients received combination gemcitabine+carboplatin while 26% (n=10) of the endometrioid cohort received combination gemcitabine+carboplatin. There was no difference between receipt of combination vs. single-agent gemcitabine in either cohort (p=0.35) and no difference in number of prior lines of therapy (p=0.6). The median time to next treatment (TNT) for the serous cohort was 3.2 months (95% CI 1.8-4.6) vs. 2.7 months (95% CI 2.2-3.2) in the endometrioid cohort (p=0.17) (FIG. 10I). There was a trend for increased median gemcitabine-specific survival in the serous cohort (15.9 months (95% CI 7.2-24.5) vs. 10.4 (95% CI 7.3-13.5) in the endometrioid cohort), but it did not reach statistical significance (p=0.37) (FIG. 10J). While these results did not reach statistical significance (likely in part due to small sample size), given the expected inferior overall survival of the USC subtype compared to the endometrioid subtype in the TCGA (FIG. 4H), these data nevertheless suggest that gemcitabine may improve outcomes for the patients with serous as opposed to endometrioid histology.

Of all patients analyzed in this cohort, the two patients with the longest TNT were of serous histology and derived significant clinical benefit from gemcitabine with TNT>16 months. The first patient was diagnosed with stage IV serous endometrial cancer in November 2016. Prior to treatment initiation, PET imaging revealed pulmonary metastasis measuring 5.2×3.2 cm with significant thoracic and abdominopelvic adenopathy. She was treated with six cycles of carboplatin+paclitaxel with excellent response and near-resolution of her pulmonary disease. She had a relatively short disease-free interval and developed disease recurrence eight months later with multiple pleural metastases, the largest of which measured 6.2×4.3 cm (FIG. 10K left). Gemcitabine+carboplatin was initiated with decreasing size of pleural lesion to 4.8×2.6 on post-cycle four imaging and continued improvement to 2.4×2.3 cm after cycle eight (FIG. 10K right). Treatment was discontinued at that time with ongoing observed response on subsequent surveillance imaging. Recurrent peritoneal disease was diagnosed a total of eleven months after discontinuation of gemcitabine+carboplatin, at which point she was re-challenged with gemcitabine+carboplatin with observed response. She is currently alive with disease on her fifth line of therapy.

A second patient was diagnosed with stage IV serous endometrial cancer in December 2013. At time of diagnosis, imaging demonstrated pelvic ascites, extensive peritoneal carcinomatosis with omental involvement, adnexal metastases, and subhepatic implant. She was treated with three cycles of neoadjuvant carboplatin+paclitaxel and underwent resection of residual disease followed by three additional cycles of carboplatin+docetaxel. Imaging at completion of therapy demonstrated persistent low-volume peritoneal carcinomatosis. First recurrence was diagnosed eight months later in the form of abdominopelvic adenopathy and multiple peritoneal implants, the largest of which was 1.6×1.4 cm in the left anterior mid-abdomen (FIG. 10L left). Gemcitabine+carboplatin was initiated at that time with resolution of adenopathy and decreasing size of peritoneal implants with resolution of prior left anterior mid-abdominal lesion on post-cycle four imaging (FIG. 10L right). She received a total of eight cycles with resolution of all implants on imaging. Recurrence was observed in the form of hepatic metastases, abdominopelvic adenopathy, and carcinomatosis nine months later, at which time gemcitabine+carboplatin was repeated with observed response. She ultimately received five total lines of therapy with progression of disease and death 4.5 years after diagnosis. These cases highlight examples where therapy with gemcitabine achieved higher therapeutic efficacy than upfront standard platinum/taxane combination.

Collectively, these data highlight the critical role of PP2A signaling in pathogenesis of uterine serous carcinoma and support repurposing as well as development of new RNR inhibitors for therapy of this aggressive histological subtype of endometrial cancer.

Discussion

The intention of experiments conducted during the course of developing embodiments for this invention was to elucidate whether highly recurrent mutations to PPP2R1A, the scaffolding subunit of PP2A, present in 40% of USC could be targeted using approved drugs. Here, we demonstrated that, indeed, mutations to the Aα subunit were predictive of sensitivity to ribonucleotide reductase (RNR) inhibitors. We further showed that patient-derived mutant cell models of USC were sensitive to RNR inhibition in vivo and the synthetic lethality could be phenocopied by inhibiting PP2A catalytic activity, and that dysregulation of PP2A was common in serous uterine tumors compared to those with endometrioid histology. Additionally, upregulation of PP2A catalytic subunit was detected in terminal xenograft tumors samples, potentially indicating that PP2A could be a regulator of RNRi therapy resistance. Finally, we presented that in a small cohort of uterine carcinoma patients treated with gemcitabine, serous patients tended to do better overall compared to endometrioid patients, in marked contrast to what is typically seen in this disease. Our analysis of the TCGA indicated that PP2A subunit expression loss was common in USC. Interestingly, B55α (PPP2R2A) expression loss was frequent in USC, occurring in almost 73% of samples.

Perhaps most importantly, our work provides clinical evidence that RNR inhibition, through the use of gemcitabine, could be beneficial to USC patients. Of all patients analyzed in our cohort, the two patients with the most durable gemcitabine response had tumors of serous origin. While advances have been made for the treatment of uterine carcinomas, new treatment options, including immunotherapy are not effective strategies for tumors of the serous subtype, and this remains a highly aggressive and devastating disease (2). Beyond USC, PP2A dysregulation is a common event in human cancer, opening the possibility of using modulators of replicative stress in a precision medicine approach for a broad range of tumor types. Collectively, the findings presented here could have immediate translational impact and alter the treatment trajectory for cancer patients.

Example II

This example provides the materials and methods utilized during the experiments described in Example I.

Cell Lines and Culture: UT42 and UT89 were generated from primary recurrent uterine serous tumors in the laboratory of Dr. Analisa DiFeo and described previously (3,21). UT89 Aα knockout cells were generated and described previously (21). OV17R was purchased from Sigma Aldrich through the European Collection of Authenticated Cell Cultures (ECACC 96020763). Mutational status of PPP2R1A in all cells were determined by Sanger sequencing. UT42, UT89, and UT185 were cultured in DMEM supplemented with 10% FBS and 1% penicillin/streptomycin. OV17 was cultured in DMEM F12 media supplemented with 5% FBS, 0.4 µg/mL hydrocortisone, 10 µg/mL insulin, and 1% penicillin/streptomycin. All cells were grown in a humidified atmosphere containing 5% $CO_2$ at 37° C. All cell lines underwent monthly testing for mycoplasma contamination.

Constructs and Lentivirus Production: pLX304-PPP2R1A plasmids were purchased from DNASU and were part of the ORFome collaboration and described previously (33). Lentivirus was generated in collaboration with the Vector Core at the University of Michigan. Following lentiviral production, virus was incubated on cells in penicillin/streptomycin free media for 24 hours, when media was replaced with normal media. After 72 hours, cells were selected in 16 µg/mL Blasticidin (Invivogen) to generate stable cell lines.

High-Throughput Compound Screening: Compound screening was completed by the Small Molecule Drug Development (SMDD) Core at Case Western Reserve University. UT42 cells, expressing EGFP or wild type Aα protein, were seeded into 384 well plates and incubated for 24 hours. After incubation, cells were treated with the Bioactives Compound Library (combination of the Selleck Chemical Library and the Sigma LOPAC Library), consisting of 3,200 compounds, at 10 µM for 72 hrs. After incubation, cell viability was determined using CellTiter-Glo, where luminescence signal is proportional to the amount of ATP present. The luminescence signal was normalized to control wells for each cell line. The normalized signal for each cell lines was graphed along the x-axis (EGFP) and y-axis (WT) to determine viability differences between the two groups. One biological replicate of the compound screening was performed, and potential hits were validated using subsequent assays and cell lines.

Compounds and Reagents: Clofarabine, Cladribine, Gemcitabine HCl, Triapine, Nelarabine, Cisplatin, and LB-100 were purchased from Selleck Chemical. In vitro use: All compounds except for LB-100 and Cisplatin were reconstituted to 40 mM in DMSO, aliquoted, and stored at –80° C. until use. LB-100 was reconstituted to 10 mM in sterile water, aliquoted, and stored at –20° C. until use. Cisplatin was reconstituted to 3 mM in sterile saline and stored at 4° C. until use. MTT was purchased from Research Products International and reconstituted to 5 mg/mL in sterile PBS, aliquoted, and stored at –20° C. until use. In vivo formulation: Clofarabine was prepared for in vivo xenografts in 25% polyethylene glycol 400 (PEG400) (Sigma Aldrich 06855) in 0.9% sterile saline (USP Sterile Grade, Fisher Scientific Z1376).

Cell Viability Assays: MTT: 2,000 cells per 96 well were plated in 100 µL of media and allowed to adhere for 24 hours at 37° C., following incubation cells were treated with increasing 2× concentrations of the appropriate compound in 100 µL to give a final concentration of 1×. After the specified incubation time at 37° C., 20 µL of 5 mg/mL MTT was added to each well and incubated at 37° C. for an additional 2 hours. Following MTT incubation, media was aspirated, and cells were dissolved in 100 µL of N-propanol. Plates were analyzed on a spectrophotometer at 570 nM and 650 nM and cell viability was calculated and $EC_{50}$ values were graphed and analyzed using Prism. Annexin/PI: Staining for flow cytometry was completed using the APC Annexin V Apoptosis Detection Kit with PI per protocol (BioLegend, 640932), and analyzed by flow cytometry at the University of Michigan Flow Cytometry Core and FlowJo software. Synergy calculations: For calculations of synergy, Compusyn Software was used (34).

Knockdown experiments: esiRNAs for RRM1, RRM2, or RLUC (control) were purchased from Sigma Aldrich and transfected at a concentration of 3000 ng esiRNA per 10 cm plate using Oligofectamine 2000 (ThermoFisher Scientific). After transfection, cells were incubated for 72 hrs. at 37° C. and subsequently harvested for protein and cell viability and knockdown was analyzed by immunoblot.

Antibodies andImmunoblotting: All antibodies used in the described studies can be found in Supplementary Table X. Proteins from whole cells were lysed in RIPA buffer (ThermoFisher Scientific) supplemented with protease and phosphatase inhibitors (Roche). Protein concentrations of cell extracts were determined using the Pierce BCA Protein Assay kit (ThermoFisher) and equal quantities of protein were separated by SDS/PAGE 12% polyacrylamide gels (Bio-Rad) and transferred to nitrocellulose membranes (Bio-Rad). Primary antibodies were detected with goat anti-mouse (Abcam) or donkey anti-rabbit (GE Healthcare) conjugated to horseradish peroxidase using the Bio-Rad ChemiDoc XRS+ or the Bio-Rad ChemiDoc MP using chemiluminescence. Densitometry quantification was performed within the Bio-Rad Image Lab software.

In vivo xenografts: UT42 cells: 10-20 million UT42 cells, expressing EGFP or wild type Aα protein, were injected subcutaneously in 5 mg/mL Matrigel (Corning 354234) into the flank of severely immunocompromised SRG rats (Sprague Dawley Rag2–/– Il2rg–/– rats from Hera BioLabs, Lexington, KY). After tumor growth to >5,000 mm³, tumors were aseptically harvested, sectioned into 2×2×2 mm fragments and implanted subcutaneously into the flank of NSG (The Jackson Laboratory; NOD.Cg-Prkdc$^{scid}$ Il2rg$^{tm1Wjl}$/SzJ) or NOG (NOD.Cg-Prkdc$^{scid}$ Il2rg$^{tm1Sug}$/JicTac; Taconic) mice using a trocar. Upon tumor growth to 150-250 mm³, mice were treated with either Vehicle Control or Clofarabine at 30 mg/kg once daily (QD) by oral gavage. In a subset of animals, tumors were allowed to grow to 500 mm³, then dosed for 3 days once daily with Vehicle Control or Clofarabine at 30 mg/kg by oral gavage before harvesting tissue for molecular analysis. Body weight was recorded three times weekly. Tumor volume was calculated as (L×W²/2), where length and width were measured with digital calipers three times weekly. After euthanasia, the tumor was collected, and half was fixed in neutral buffered formalin and half was flash frozen in liquid nitrogen. UT89 cells: Animal studies were approved by the Institutional Animal Care and Use Committee (IACUC) at The University of Michigan. Animal use and care was in strict compliance with institutional guidelines and all experiments conformed to the relevant regulatory standards by The University of Michigan. 1 million UT89 cells were injected subcutaneously into the flanks of 6-8 week old female NCI nude mice in 50% Matrigel (Corning 354234). Tumor volumes were assessed by caliper measurement (L×W²/2). Upon tumor growth to 150-250 mm³, mice were randomized and given Vehicle Control or Clofarabine at 30 mg/kg once daily (QD) by oral gavage. Tumor tissue was both formalin-fixed and snap frozen in liquid nitrogen for analysis. OV17R cells: 5 million and 10 million cells were injected subcutaneously into the flanks of 6-8 week old female Nod Scid Gamma mice in 50% Matrigel (Corning 354234). No tumors formed, so this cell line was not used for in vivo studies.

Immunocytochemistry: Cells were plated on 4 chamber cell culture slides (CellTreat 229164) and treated with control or compound containing media for specified times. Prepared slides were imaged at the University of Michigan Microscopy Core, using the Zeiss Apotome. Quantification of the images was performed using Image J, scale bar on images represents 50 µm.

TCGA Data Analysis: TCGA PanCancer Atlas data was accessed through cBioPortal. Loss of PP2A subunit expression or mutation of PP2A subunits were calculated from TCGA data where copy number and mutation data were available (n=109, Uterine Serous Carcinomas; n=399 Endometrioid Uterine Carcinomas, analyzed on cBioPortal). Kaplan-Meier analysis of overall surviaval in Serous or Endometrioid uterine carcinoma patients with recurrent disease were downloaded and analyzed via GraphPad Prism, Log-rank (Mantel-Cox) test was used to calculate p-value.

MSKCC Cohort Analysis: Patient selection: Patients with recurrent endometrial cancer who received gemcitabine from December 2010 to December 2019 at Memorial Sloan Kettering Cancer Center (MSKCC) were retrospectively analyzed and followed until Apr. 20, 2020. Patient clinical characteristics including histology, tumor grade, stage at diagnosis, treatment history including prior chemotherapy, tumor genomic profiling results, and outcomes were abstracted from the medical record. The study was approved by the Institutional Review Board at MSKCC. Statistical analysis: Baseline clinical and disease characteristics were summarized as medians and ranges for continuous variables and as numbers and percentages for categorical variables. Fisher's exact test or Mann-Whitney U test was used for analysis as appropriate. A two-tailed p-value of less than 0.05 was considered statistically significant. Kaplan-Meier survival analysis was used to determine time to next treatment (TNT) and gemcitabine-specific survival. Time was calculated from initiation of gemcitabine to start of next therapy or hospice for TNT and from initiation of gemcitabine to death from any cause for gemcitabine-specific survival. For patients that received gemcitabine more than once, their first course was used for analysis. All statistical analyses were performed using SPSS (version 14.0; SPSS, Inc, Chicago, Ill., USA).

INCORPORATION BY REFERENCE

The entire disclosure of each of the patent documents and scientific articles referred to herein is incorporated by reference for all purposes.

The following references, which are numerically denoted herein, are incorporated by reference in their entireties:

1. Siegel R L, Miller K D, Jemal A. Cancer statistics, 2018. CA Cancer J Clin 2018; 68(1):7-30 doi 10.3322/caac.21442.
2. Urick M E, Bell D W. Clinical actionability of molecular targets in endometrial cancer. Nat Rev Cancer 2019; 19(9):510-21 doi 10.1038/s41568-019-0177-x.
3. Taylor S E, O'Connor C M, Wang Z, Shen G, Song H, Leonard D, et al. The highly recurrent PP2A Aalpha-subunit mutation P179R alters protein structure and impairs PP2A enzyme function to promote endometrial tumorigenesis. Cancer research 2019 doi 10.1158/0008-5472.can-19-0218.
4. Jeong A L, Han S, Lee S, Su Park J, Lu Y, Yu S, et al. Patient derived mutation W257G of PPP2R1A enhances cancer cell migration through SRC-JNK-c-Jun pathway. Scientific reports 2016; 6:27391 doi 10.1038/srep27391.
5. Haesen D, Abbasi Asbagh L, Derua R, Hubert A, Schrauwen S, Hoorne Y, et al. Recurrent PPP2R1A Mutations in Uterine Cancer Act through a Dominant-Negative Mechanism to Promote Malignant Cell Growth. Cancer research 2016; 76(19):5719-31 doi 10.1158/0008-5472.can-15-3342.
6. Gibson W J, Hoivik E A, Halle M K, Taylor-Weiner A, Cherniack A D, Berg A, et al. The genomic landscape and evolution of endometrial carcinoma progression and abdominopelvic metastasis. Nat Genet 2016; 48(8): 848-55 doi 10.1038/ng.3602.
7. Sangodkar J, Farrington C C, McClinch K, Galsky M D, Kastrinsky D B, Narla G. All roads lead to PP2A: exploiting the therapeutic potential of this phosphatase. The FEBS journal 2016; 283(6):1004-24 doi 10.1111/febs.13573.
8. O'Connor C M, Perl A, Leonard D, Sangodkar J, Narla G. Therapeutic Targeting of PP2A. The international journal of biochemistry & cell biology 2018; 96:182-93 doi 10.1016/j.biocel.2017.10.008.
9. Chen W, Arroyo J D, Timmons J C, Possemato R, Hahn W C. Cancer-associated PP2A Aalpha subunits induce functional haploinsufficiency and tumorigenicity. Cancer research 2005; 65(18):8183-92 doi 10.1158/0008-5472.can-05-1103.
10. Sablina A A, Hector M, Colpaert N, Hahn W C. Identification of PP2A complexes and pathways involved in cell transformation. Cancer research 2010; 70(24):10474-84 doi 10.1158/0008-5472.can-10-2855.
11. Chen W, Possemato R, Campbell K T, Plattner C A, Pallas D C, Hahn W C. Identification of specific PP2A complexes involved in human cell transformation. Cancer Cell 2004; 5(2):127-36.
12. Sablina A A, Hahn W C. The Role of PP2A A Subunits in Tumor Suppression. Cell Adh Migr. Volume 12007. p 140-1.
13. Jackson J B, Pallas D C. Circumventing Cellular Control of PP2A by Methylation Promotes Transformation in an Akt-Dependent Manner1. Neoplasia (New York, NY). Volume 142012. p 585-99.
14. Pallas D C, Shahrik L K, Martin B L, Jaspers S, Miller T B, Brautigan D L, et al. Polyoma small and middle T antigens and SV40 small t antigen form stable complexes with protein phosphatase 2A. Cell 1990; 60(1): 167-76.
15. Cho U S, Xu W. Crystal structure of a protein phosphatase 2A heterotrimeric holoenzyme. Nature 2007; 445(7123):53-7 doi 10.1038/nature05351.
16. Shi Y. Serine/threonine phosphatases: mechanism through structure. Cell 2009; 139(3):468-84 doi 10.1016/j.cell.2009.10.006.
17. O'Connor C M, Leonard D, Wiredja D, Avelar R A, Wang Z, Schlatzer D, et al. Inactivation of PP2A by a 18. Ruediger R, Zhou J, Walter G. Mutagenesis and expression of the scaffolding Aalpha and Abeta subunits of PP2A: assays for measuring defects in binding of cancer-related Aalpha and Abeta mutants to the regulatory B and catalytic C subunits. Methods in molecular biology (Clifton, NJ) 2007; 365:85-99 doi 10.1385/1-59745-267-x:85.
19. Wisitpitthaya S, Zhao Y, Long M J, Li M, Fletcher E A, Blessing W A, et al. Cladribine and Fludarabine Nucleotides Induce Distinct Hexamers Defining a Common Mode of Reversible RNR Inhibition. ACS Chem Biol 2016; 11(7):2021-32 doi 10.1021/acschembio.6b00303.
20. Aye Y, Stubbe J. Clofarabine 5'-di and -triphosphates inhibit human ribonucleotide reductase by altering the quaternary structure of its large subunit. Proc Natl Acad Sci USA 2011; 108(24):9815-20 doi 10.1073/pnas.1013274108.
21. O'Connor C M, Hoffa M T, Taylor S E, Avelar R A, Narla G. Protein phosphatase 2A Aalpha regulates Abeta protein expression and stability. The Journal of biological chemistry 2019 doi 10.1074/jbc.RA119.007593.
22. Parker W B. Enzymology of Purine and Pyrimidine Antimetabolites Used in the Treatment of Cancer. Chemical Reviews 2009; 7(109):2880-93 doi 10.1021/cr900028p.
23. Noto F K, Adjan-Steffey V, Tong M, Ravichandran K, Zhang W, Arey A, et al. Sprague Dawley Rag2 null rats created from engineered spermatogonial stem cells are immunodeficient and permissive to human xenografts. Mol Cancer Ther 2018; 17(11):2481-9 doi 10.1158/1535-7163.mct-18-0156.
24. Noto F K, Sangodkar J, Adedeji B T, Moody S, McClain C B, Tong M, et al. The SRG rat, a Sprague-Dawley Rag2/Il2rg double-knockout validated for human tumor oncology studies. PloS one 2020; 15(10): e0240169 doi 10.1371/journal.pone.0240169.
25. Aye Y, Li M, Long M J, Weiss R S. Ribonucleotide reductase and cancer: biological mechanisms and targeted therapies. Oncogene 2015; 34(16):2011-21 doi 10.1038/onc.2014.155.
26. Zhao S, Choi M, Overton J D, Bellone S, Roque D M, Cocco E, et al. Landscape of somatic single-nucleotide and copy-number mutations in uterine serous carcinoma. Proc Natl Acad Sci USA 2013; 110(8):2916-21 doi 10.1073/pnas.1222577110.
27. Leskela S, Perez-Mies B, Rosa-Rosa J M, Cristobal E, Biscuola M, Palacios-Berraquero M L, et al. Molecular Basis of Tumor Heterogeneity in Endometrial Carcinosarcoma. Cancers (Basel) 2019; 11(7) doi 10.3390/cancers11070964.
28. Kandoth C, Schultz N, Cherniack A D, Akbani R, Liu Y, Shen H, et al. Integrated genomic characterization of endometrial carcinoma. Nature 2013; 497(7447):67-73 doi 10.1038/nature12113.
29. Liu J, Lichtenberg T, Hoadley K A, Poisson L M, Lazar A J, Cherniack A D, et al. An Integrated TCGA Pan-Cancer Clinical Data Resource to Drive High-Quality Survival Outcome Analytics. Cell 2018; 173 (2):400-16 e11 doi 10.1016/j.cell.2018.02.052.
30. Berger A C, Korkut A, Kanchi R S, Hegde A M, Lenoir W, Liu W, et al. A Comprehensive Pan-Cancer Molecular Study of Gynecologic and Breast Cancers. Cancer Cell 2018; 33(4):690-705 e9 doi 10.1016/j.ccell.2018.03.014.
31. Qiu Z, Fa P, Liu T, Prasad C B, Ma S, Hong Z, et al. A Genome-Wide Pooled shRNA Screen Identifies PPP2R2A as a Predictive Biomarker for the Response to ATR and CHK1 Inhibitors. Cancer research 2020; 80(16):3305-18 doi 10.1158/0008-5472.CAN-20-0057.
32. Kalev P, Simicek M, Vazquez I, Munck S, Chen L, Soin T, et al. Loss of PPP2R2A inhibits homologous recombination DNA repair and predicts tumor sensitivity to PARP inhibition. Cancer research 2012; 72(24):6414-24 doi 10.1158/0008-5472.CAN-12-1667.
33. Yang X, Boehm J S, Salehi-Ashtiani K, Hao T, Shen Y, Lubonja R, et al. A public genome-scale lentiviral expression library of human ORFs. Nat Methods 2011; 8(8):659-61 doi 10.1038/nmeth.1638.
34. Chou T C. Theoretical basis, experimental design, and computerized simulation of synergism and antagonism in drug combination studies. Pharmacol Rev 2006; 58(3):621-81 doi 10.1124/pr.58.3.10.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of treating uterine serous carcinoma in a subject, comprising:
   detecting in a sample obtained from the subject a P179R and/or S256 mutation within the PPP2R1A subunit of the PP2A gene, wherein the presence of the mutation in the subject indicates a high grade uterine serous carcinoma; and
   treating the subject having a P179R and/or S256 mutation within the PPP2R1A subunit of the PP2A gene by administering to the subject a ribonucleotide reductase inhibitor selected from clofarabine and cladribine.

2. A method, comprising:
   (a) evaluating a sample containing nucleic acids obtained from a subject having uterine serous carcinoma to detect the presence of one or more mutations in the PPP2R1A subunit of the PP2A gene, wherein evaluating comprises hybridizing to a PPP2R1A subunit of the PP2A gene nucleic acid an oligonucleotide comprising a nucleotide sequence complementary with one or more PPP2R1A subunit of the PP2A gene mutations, wherein the one or more PPP2R1A subunit of the PP2A gene mutations are nucleic acid sequence mutations selected from the group consisting of P179R or S256F;
   (b) detecting a P179R or S256F mutation in the PPP2R1A subunit of the PP2A gene in the sample; and
   (b) administering a treatment to the subject having the mutation within the PPP2R1A subunit of the PP2A gene, wherein the treatment comprises administration to the subject a ribonucleotide reductase inhibitor selected from clofarabine and cladribine.

3. The method of claim 2, wherein said nucleic acid from the individual is RNA and the PPP2R1A subunit of the PP2A nucleic acid is cDNA.

4. The method of claim 2, wherein said sample is selected from the group consisting of blood, serum, and plasma.

5. The method of claim 2, wherein the sample is a uterine tumor tissue sample.

* * * * *